US009895484B2

(12) United States Patent
Pollard et al.

(10) Patent No.: US 9,895,484 B2
(45) Date of Patent: Feb. 20, 2018

(54) INJECTOR SYSTEM

(71) Applicant: Liebel-Flarsheim Company LLC, Cincinnati, OH (US)

(72) Inventors: Pamela L. Pollard, Dardenne Prairie, MO (US); Robert J. McGraw, Cincinnati, OH (US); John E. Powers, Wildwood, MO (US); Richard A. Hoyt, Webster Groves, MO (US); Robert J. Ziemba, Cincinnati, OH (US); Bina A. Soni, Loveland, OH (US)

(73) Assignee: LIEBEL-FLARSHEIM COMPANY LLC, Cincinnati, OH (US)

( * ) Notice: Subject to any disclaimer, the term of this patent is extended or adjusted under 35 U.S.C. 154(b) by 288 days.

(21) Appl. No.: 14/376,533

(22) PCT Filed: Feb. 19, 2013

(86) PCT No.: PCT/US2013/026627
§ 371 (c)(1),
(2) Date: Aug. 4, 2014

(87) PCT Pub. No.: WO2013/126318
PCT Pub. Date: Aug. 29, 2013

(65) Prior Publication Data
US 2015/0025375 A1 Jan. 22, 2015

Related U.S. Application Data

(60) Provisional application No. 61/601,599, filed on Feb. 22, 2012.

(51) Int. Cl.
G06F 13/00 (2006.01)
A61M 5/00 (2006.01)
(Continued)

(52) U.S. Cl.
CPC ........ *A61M 5/007* (2013.01); *A61M 5/14546* (2013.01); *G06F 19/3406* (2013.01);
(Continued)

(58) Field of Classification Search
CPC .............. A61M 5/14546; A61M 5/007; A61M 5/16827; G06F 19/3468; G06F 19/3462
(Continued)

(56) References Cited

U.S. PATENT DOCUMENTS 5,687,717 A * 11/1997 Halpern ............... A61B 5/0205
128/903
6,673,033 B1 * 1/2004 Sciulli ............... A61M 5/14546
604/123

(Continued)

FOREIGN PATENT DOCUMENTS

WO 2007/062315 A2 5/2007
WO 2008/083313 A2 7/2008

*Primary Examiner* — Faisal M Zaman
(74) *Attorney, Agent, or Firm* — Marsh Fischmann & Breyfogle LLP

(57) ABSTRACT

Multiple embodiments of contrast media injector systems (800, 800', 800c) are disclosed. A number of different devices are disclosed for providing user input to such a contrast media injector system (800, 800', 800c), including at least one tablet computer (700), a user-mountable user input device (760), a smartphone (762), and various combinations thereof.

21 Claims, 17 Drawing Sheets

(51) Int. Cl.
*A61M 5/145* (2006.01)
*G06F 19/00* (2011.01)

(52) U.S. Cl.
CPC ..... *G06F 19/3468* (2013.01); *A61M 2205/50* (2013.01); *A61M 2205/505* (2013.01); *A61M 2205/52* (2013.01); *A61M 2209/01* (2013.01); *A61M 2209/082* (2013.01); *A61M 2209/086* (2013.01)

(58) Field of Classification Search
USPC .................................................. 710/303, 304
See application file for complete search history.

(56) References Cited

U.S. PATENT DOCUMENTS

| | | | | |
|---|---|---|---|---|
| 2004/0027337 A1* | 2/2004 | Hunt | ..................... | G06F 1/1626 345/173 |
| 2006/0079768 A1* | 4/2006 | Small | ................ | A61M 5/14546 600/432 |
| 2008/0306443 A1* | 12/2008 | Neer | ..................... | A61M 5/007 604/121 |
| 2010/0030387 A1* | 2/2010 | Sen | ................... | A61M 5/14232 700/282 |
| 2010/0293496 A1* | 11/2010 | Lafferty | ............ | A61M 5/14546 715/772 |
| 2011/0021905 A1* | 1/2011 | Patrick | ..................... | A61B 8/00 600/424 |
| 2011/0137160 A1* | 6/2011 | Fago | ..................... | A61M 5/007 600/432 |
| 2011/0137161 A1* | 6/2011 | Kasako | ............... | G06F 19/3468 600/432 |
| 2011/0137251 A1* | 6/2011 | McLean | ............ | A61M 5/14546 604/154 |
| 2011/0178359 A1* | 7/2011 | Hirschman | ............ | A61B 6/037 600/4 |
| 2011/0218434 A1* | 9/2011 | Ziemba | ............... | G06F 19/3468 600/432 |

* cited by examiner

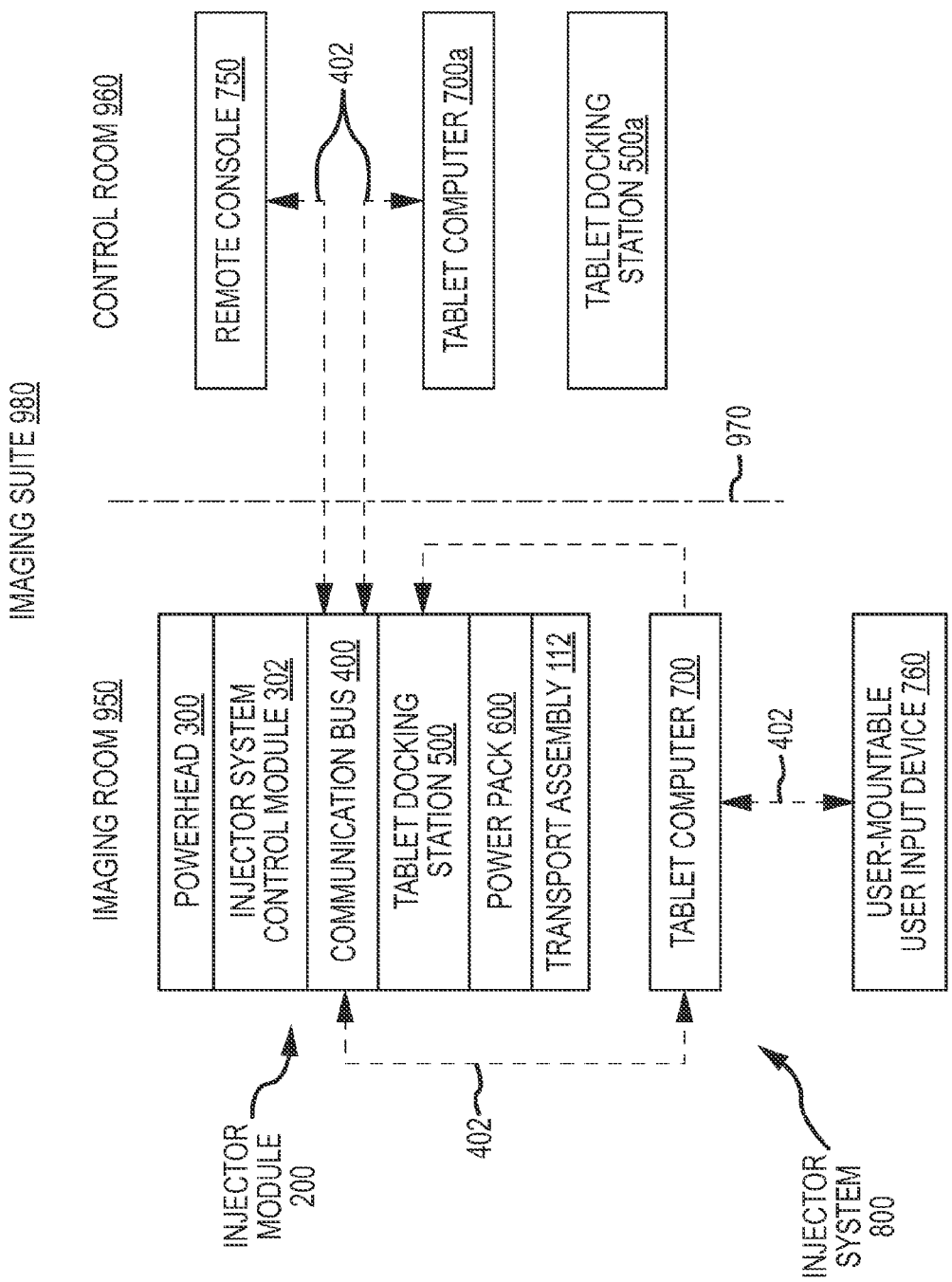

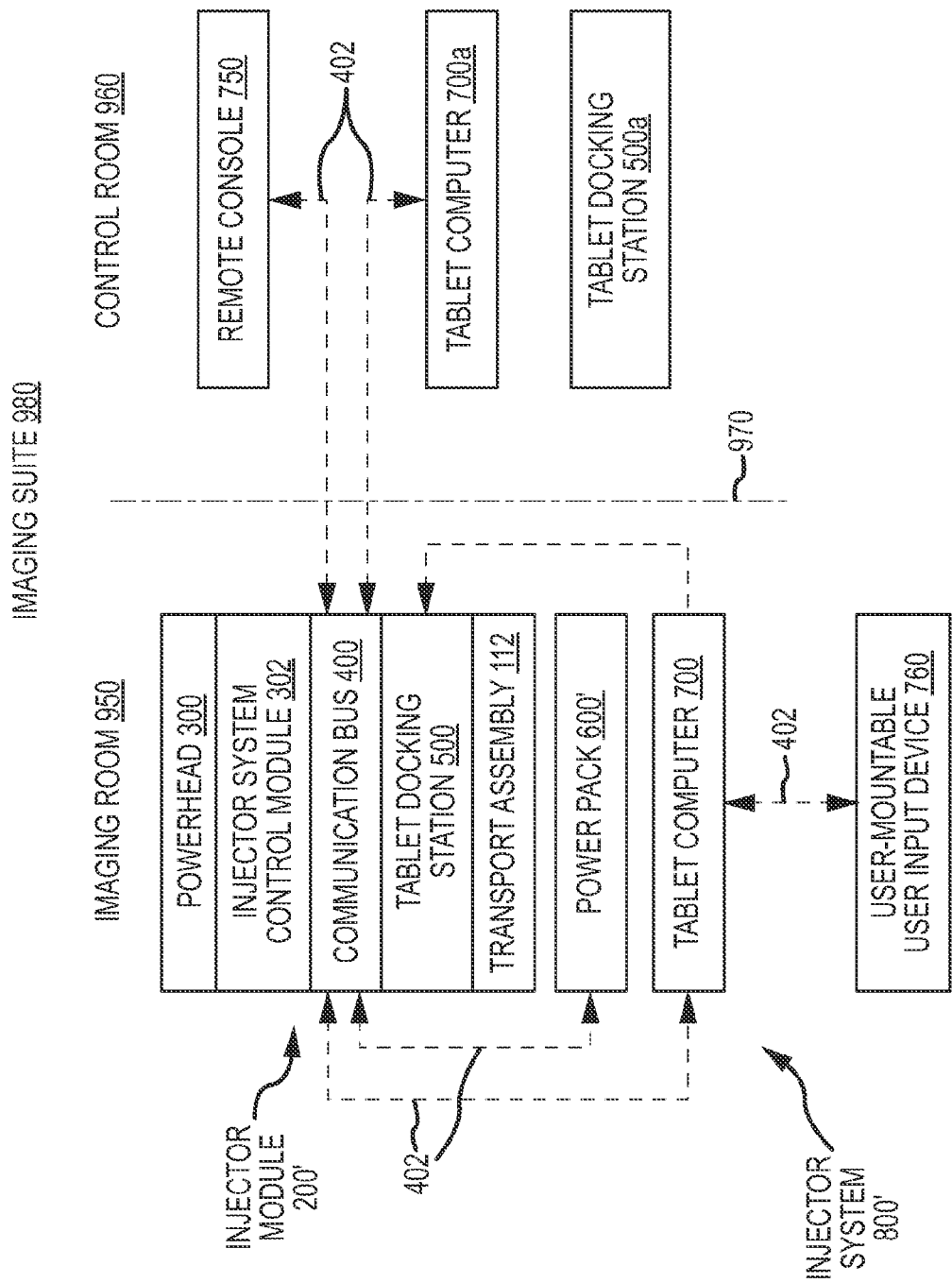

INJECTOR SYSTEM

CROSS-REFERENCE TO RELATED APPLICATIONS

This patent application is a U.S. National Stage of PCT/US2013/026627, filed Feb. 19, 2013, which is a nonprovisional patent application of and claims priority to U.S. Provisional Patent Application Ser. No. 61/601,599, that is entitled "INJECTOR SYSTEM," and that was filed on 22 Feb. 2012. The entire disclosure of each application set forth in this "CROSS REFERENCE TO RELATED APPLICATIONS" section is hereby incorporated by reference.

FIELD OF THE INVENTION

The present invention generally pertains to contrast media injector systems and, more particularly, to input devices that may be used with such contrast media injector systems.

BACKGROUND

Various medical procedures require that one or more medical fluids be injected into a patient. For example, medical imaging procedures oftentimes involve the injection of contrast media into a patient, possibly along with saline and/or other fluids. Other medical procedures involve injecting one or more fluids into a patient for therapeutic purposes. Power injectors may be used for these types of applications.

A power injector generally includes what is commonly referred to as a powerhead. One or more syringes may be mounted to the powerhead in various manners (e.g., detachably; rear-loading; front-loading; side-loading). Each syringe typically includes what may be characterized as a syringe plunger, piston, or the like. Each such syringe plunger is designed to interface with (e.g., contact and/or temporarily interconnect with) an appropriate syringe plunger driver that is incorporated into the powerhead, such that operation of the syringe plunger driver axially advances the associated syringe plunger inside and relative to a barrel of the syringe. One typical syringe plunger driver is in the form of a ram that is mounted on a threaded lead or drive screw. Rotation of the drive screw in one rotational direction advances the associated ram in one axial direction, while rotation of the drive screw in the opposite rotational direction advances the associated ram in the opposite axial direction.

SUMMARY

A first aspect of the present invention is embodied by a contrast media injector system that includes an injector module, an injector system control module, and at least one tablet computer. The injector module includes a drive source and a first tablet docking station. The injector system control module is in communication with the drive source. The tablet computer is connectable to the first tablet docking station of the injector module and includes at least one user input device in communication with the injector system control module. When the tablet computer is connected to the first tablet docking station, it may be characterized as having become part of the injector module.

A number of feature refinements and additional features are applicable to the first aspect of the present invention. These feature refinements and additional features may be used individually or in any combination. The following discussion is applicable to the first aspect, up to the start of the discussion of a second aspect of the present invention.

The injector module may include a powerhead. This powerhead may itself incorporate at least one user input device of any appropriate type (e.g., touchscreen, keyboard, touch pad, mouse, trackball, barcode reader/receiver). When a tablet computer is connected or docked to the first tablet docking station, this tablet computer may block access to at least one user input device, including where the tablet computer blocks access to each user input device (other than the tablet computer) incorporated by the injector module. Consider the case where the powerhead incorporates both the first tablet docking station and a touchscreen. In this configuration, a tablet computer of the contrast media injector system may preclude use of the powerhead touchscreen when it is connected to the first tablet docking station. In one embodiment the injector module may have only a single user input device in the form of a tablet computer when this tablet computer is connected to the tablet docking station (e.g., in the form of a touchscreen of the tablet computer). Another embodiment is directed to the contrast media injector system having a single user input device in the form of a tablet computer, whether this tablet computer is docked to or removed from the first tablet docking station of the injector module (e.g., the injector system does not include a remote console or any user input device on a powerhead of the injector module in this embodiment).

The first tablet docking station may be incorporated in any appropriate manner by the injector module. One embodiment has the first tablet docking station be incorporated by the injector module so that docking a tablet computer thereto blocks access to at least one user input device of the injector module (e.g., blocks access to a touchscreen of a powerhead). Another embodiment has the first tablet docking station be incorporated by the injector module so as to not interfere with the operation of at least one user input device for the injector module (e.g., a touchscreen on a powerhead may be available to accept user input when the tablet computer is docked to the first tablet docking station).

A second aspect of the present invention is embodied by a contrast media injector system that includes an injector module, an injector system control module, and at least one tablet computer. The injector module includes a drive source. The injector system control module is in communication with the drive source. The tablet computer includes at least one user input device in communication with the injector system control module. All user inputs to the injector system control module are provided only through one or more tablet computers of the injector system in the case of the second aspect.

A number of feature refinements and additional features are applicable to the second aspect of the present invention. These feature refinements and additional features may be used individually or in any combination. The following discussion is applicable to at least the second aspect, up to the start of the discussion of a third aspect of the present invention.

The injector module may include a powerhead. This powerhead may be configured so as to not incorporate a user input device of any type. The contrast media injector system also may not utilize a remote console. In each such instance, all user inputs to the injector system control module are required to be entered through a tablet computer of the contrast media injector system in the case of the second aspect (although more than one tablet computer could be used by the injector system).

A third aspect of the present invention is embodied by a contrast media injector system that includes an injector module, an injector system control module, a first computer, and a user-mountable user input device. The injector module includes a drive source. The injector system control module is in communication with the drive source. The first computer is in communication with the injector system control module. The user-mountable user input device is in communication with the first computer, and may be mounted/attached to a user in any appropriate manner.

A number of feature refinements and additional features are applicable to the third aspect of the present invention. These feature refinements and additional features may be used individually or in any combination. The following discussion is applicable to at least the third aspect.

The first computer may be incorporated by a powerhead of the injector module, may be in the form of a remote console that is physically separate from the injector module, or may be in the form of a tablet computer. The user-mountable user input device may include at least one user mounting connector (e.g., a strap, belt, sleeve, or the like for attaching a user input device to a user/operator of the injector system, for instance on an arm or a wrist of the user). In one embodiment, the user-mountable user input device is in the form of a smart phone (e.g., having a touchscreen for accepting user input) that is at least partially contained in some type of casing, jacket, or the like that is appropriately mounted/attached to a user. In any case, such a user input device allows a user to have both hands available for executing any appropriate task in relation to an imaging/injection procedure. Such a user input device should also allow a user to move more freely about an imaging room or the like during an imaging/injection procedure. The user may utilize the now user-mounted user input device to provide user input to the first computer of the contrast media injector system, which in turn then communicates with the injector system control module of an injector module (e.g., the user-mounted user input device may be used to control operation of and/or provide user input to an injector module through communication with its injector system control module, but only indirectly through the first computer).

A number of feature refinements and additional features are separately applicable to each of above-noted first, second, and third aspects of the present invention as well. These feature refinements and additional features may be used individually or in any combination in relation to each of the first, second, and third aspects.

The contrast media injector system may utilize at least one tablet computer. One embodiment has the injector system utilizing a plurality of tablet computers. Any appropriate number of tablet computers may be utilized. Each such tablet computer may be used to communicate with the injector system control module of one or more injector modules.

The injector module itself may include a first tablet docking station. This first tablet docking station may be incorporated by a powerhead of the injector module, or may be incorporated by the injector module at another location (e.g., mounted on a support, where the powerhead may be movably interconnected with this same support). Multiple tablet docking stations may be utilized by the injector system. At least one tablet computer may be both docked to and removed from each of these tablet docking stations. A first tablet docking station may be located in a first room (e.g., an imaging room; co-located with an injector module), while a second tablet docking station may be located in a different second room (e.g., a control room). The injector module of the third aspect may incorporate the first tablet docking station in the manner discussed above in relation to the first aspect. The second tablet docking station may be physically separated from this injector module. In one embodiment where there are first and second tablet docking stations, a first tablet computer is dedicated to the first tablet docking station and a second tablet computer is dedicated to the second tablet docking station. In another embodiment where there are first and second tablet docking stations, the injector system may use a single tablet computer.

The contrast media injector system may include a plurality of the injector modules described herein. Any appropriate number of injector modules may be utilized. Each injector module may be disposed at any appropriate location. In one embodiment, a given tablet computer may be used to communicate with and/or control operation of two or more injector modules. For instance, a tablet computer may be used in conjunction with a first injector module in a first imaging room, and may be transported (e.g., carried by a user) to a second imaging room for use in conjunction with a second injector module.

The contrast media injector system may utilize at least one user-mountable user input device for communicating with one or more tablet computers used by the contrast media injector system. A given user-mountable user input device may include at least one user mounting connector (e.g., a strap, belt, sleeve, or the like for attaching a user input device to a user/operator of the injector system, for instance on an arm or a wrist of the user). In one embodiment, the user-mountable user input device is in the form of a smart phone (e.g., having a touchscreen for accepting user input) that is at least partially contained in some type of casing, jacket, or the like that is appropriately mounted/attached to a user. This smart phone may be used to program an injection protocol, to initiate an injection by the injector system, to terminate the execution of an injection by the injector system, or any combination thereof. Injection results of any appropriate type may be displayed on the smart phone. In any case, such a user input device allows a user to have both hands available for executing any appropriate task in relation to an imaging/injection procedure. Such a user input device should also allow a user to move more freely about an imaging room or the like during an imaging/injection procedure.

The user may utilize what is now a user-mounted user input device to provide user input to a tablet computer of the contrast media injector system, which in turn then communicates with the injector system control module of an injector module (e.g., the user-mounted user input device may be used to control operation of and/or provide user input to an injector module through communication with its injector system control module, but only indirectly through a tablet computer). This still satisfies the requirement of the second aspect that all inputs to the injector system control module be provided through a tablet computer (i.e., the second aspect does not require al inputs to be made directly to a tablet computer; the second aspect covers providing inputs to the injector system control module that are entered at a user-mounted user input device, which are transmitted to a tablet computer, and which are then transmitted to the injector system control module—a tablet computer may be part of the communication link between a user-mountable user input device and an injector module).

The tablet computer may incorporate a touchscreen to accommodate user input to the injector module, and including the powerhead. Any appropriate way of accommodating user input through a touchscreen on the tablet computer may be utilized. For instance, buttons or the like may be displayed on the touchscreen of the tablet computer to accommodate user input (e.g., via touching the same). An electronic keyboard may be displayed on the touchscreen for providing user input to the injector module. This tablet computer may be used to program an injection protocol, to initiate an injection by the injector system, to terminate the execution of an injection by the injector system, or any combination thereof. Injection results of any appropriate type may be displayed on this tablet computer.

One tablet computer could be connected to a tablet docking station incorporated by an injector module and could allow a user to provide inputs to the injector module. At least one other tablet computer may be physically disconnected from the injector module and also may be used to provide inputs to the injector module (e.g., a tablet computer located in a control room that is isolated in at least some respect from the injector module (which may be in an imaging room or the like with a tablet computer docked thereto)). The contrast media injector system may be configured such that no tablet computer need be docked to the injector module for execution of an injection protocol by the injector system (although it may be that at least one tablet computer needs to be in communication with the injector module).

One or more tablet docking stations of any appropriate type and in any appropriate location on the injector module may be utilized by the contrast media injector system. One option is for a powerhead of the injector module to incorporate the tablet docking station. The tablet docking station may be incorporated on a surface of a powerhead that incorporates its own touchscreen or other user input device(s). Other locations on the injector module may be appropriate for the tablet docking station (e.g., including where the powerhead does not incorporate the tablet docking station). The tablet docking station may be completely separate from the powerhead. For instance, the tablet docking station may be incorporated so as to not move along with the powerhead when tilting the powerhead for fluid loading and/or injection operations. The tablet docking station may be incorporated by a frame for the injector module. A separate platform may be mounted to and/or suspended from a stand to which the powerhead is pivotally interconnected, where this platform incorporates the tablet docking station.

The tablet docking station may include at least one port or connector for providing an interface between a tablet computer and the injector module. A tablet computer may be powered by the injector module when connected to the tablet docking station (e.g., one or more ports or connectors could accommodate power transmission to a docked tablet computer). The tablet docking station could incorporate one or more ports or connectors for establishing a communication ink between a docked tablet computer and the injector module (e.g., for transmission of data and/or commands) when a tablet computer is connected to the tablet docking station. However, in one embodiment at least one tablet computer of the injector system is able to communicate with the injector module, whether or not the tablet computer(s) is connected to the tablet docking station. For instance, at least one tablet computer of the injector system may include a wireless communications module to allow the tablet computer to communicate wirelessly with the injector module.

A fourth aspect of the present invention is embodied by a contrast media injector system that includes an injector module, an injector system control module, and least one smart phone. The injector module includes at least one drive source. The injector system control module is in communication with at least one drive source of the injector module. The smart phone is configured to communicate with the injector system control module.

A number of feature refinements and additional features are applicable to the fourth aspect of the present invention. These feature refinements and additional features may be used individually or in any combination. The following discussion is applicable to at least the fourth aspect.

A first computer may be configured to communicate with the injector system control module (including in addition to the smart phone). One embodiment has this first computer being incorporated by the injector module (e.g., by a powerhead of the injector module). Another embodiment has this first computer being a remote console that is physically separate from the injector module. Yet another embodiment has this first computer being a tablet computer. Multiple computers (including in addition to the smart phone) may be utilized by the injector system.

The smart phone may be configured to communicate directly with the injector system control module. Another option is for the smart phone to be configured so as to communicate with another computer (e.g., a computer incorporated by an injector module, a tablet computer, a remote console), which then in turn communicates with the injector system control module.

The injector system may include at least one tablet computer, and thereby encompasses using multiple tablet computers. The discussion presented above in relation to the first, second, and third aspects regarding a tablet computer for an injector system is therefore equally applicable to this fourth aspect. In the case of the fourth aspect, each tablet computer and each smart phone could be configured to communicate directly with the injector system control module of a given injector module, or a smart phone could be configured so as to communicate with a tablet computer, which then in turn communicates with the injector system control module.

A number of feature refinements and additional features are separately applicable to each of above-noted first, second, third, and fourth aspects of the present invention as well. These feature refinements and additional features may be used individually or in any combination in relation to each of the first, second, third, and fourth aspects.

Each injector module of an injector system may be of any appropriate configuration. For instance, a given injector module could be in the form of a power injector. One or more syringes may be mounted to the power injector in any appropriate manner. A given injector module could be of a configuration that utilizes one or more peristaltic pumps of any appropriate type (e.g., rotary or linear; a "syringe-less" configuration).

Any appropriate drive source may be utilized by each injector module of an injector system. Multiple drive sources may be utilized by a given injector module. Generally, this drive source provides at least part of the force used to transfer one or more fluids from the injector module in any appropriate manner. Representative drive source forms include a brushed or brushless electric motor, a hydraulic motor, a pneumatic motor, a piezoelectric motor, or a stepper motor. One or more drive sources may interface/interact with one or more other components to affect fluid transfer from a given injector module. For instance, the injector module may include one or more syringe plunger drivers (e.g., of a power injector) that are each responsive to operation of one or more drive sources (e.g., one or more drive sources may be used to move the syringe plunger driver in a desired manner, for instance in at least one direction along an axial path). One or more drive sources may be part of and/or utilized by a peristaltic pump of any appropriate type (and which may "pump" fluid from a given injector module).

An injector module of an injector system may include a support and a powerhead that is movably connected with the support (e.g., pivotable about a certain axis relative to this support), including where the powerhead includes at least one syringe plunger driver. This support could be in the form of an extendable/retractable arm. One embodiment has this support being appropriately anchored to the floor, a wall, or a ceiling. Another embodiment has this support being anchored to a base (e.g., that incorporates a transport assembly such that the injector module is portable). Yet another embodiment has the injector module (e.g., its powerhead) being attached to or otherwise incorporated by a scanner gantry, a patient bed, an IV pole, or the like.

The injector module may be characterized as including a frame. This frame in turn may be characterized as being a primary supporting structure for the remainder of the injector module. The frame may be of any appropriate size, shape, configuration, and/or type. In one embodiment, the frame includes a base and a support (e.g., an at least generally vertically extending pole, stand, or the like) that extends from the base. The injector module may include a powerhead that may be interconnected with this support in any appropriate manner, for instance to allow the powerhead to be rotated, pivoted, and/or tilted relative to the support about a certain axis (e.g., for fluid loading and fluid discharge operations). The powerhead may be appropriately mounted (directly or indirectly) to the support so as to be disposed at a higher elevation than the base.

The injector module may include a transport assembly (e.g., incorporated by the above-noted base) to provide portability for the injector module (e.g., at least generally in the form of a cart). Such a transport assembly allows an entirety of the injector module to be moved from one location to another. The transport assembly may be of any appropriate type, for instance in the form of a plurality of individual transport members. These transport members may be of any appropriate size, shape, configuration, and/or type, for instance casters, rollers, wheels, sides, tracks, or the like. One or more locks could be utilized to selectively maintain the injector module in a fixed position relative to its supporting surface (e.g., to temporarily disable the transport assembly; for execution of an injection protocol by the injector system, which may be done in conjunction with an imaging operation).

Any powerhead utilized by an injector module of an injector system may be of any appropriate configuration, for instance being of a single-head type (e.g., to accommodate a single syringe) or being of a multi-head type (e.g., to accommodate multiple syringes). Any appropriate syringe mount may be used by the powerhead to provide an interface between the powerhead and a corresponding syringe (e.g., a faceplate, fixed mount, a fixed mount in combination with an adapter). This powerhead may be incorporated in any appropriate manner. For instance, the powerhead (including an entirety of the injector module) may be incorporated in any appropriate manner by a scanner gantry, by a patient bed, by an IV pole, by a transportable cart, by a floor/wall/ceiling mounted system, or the like.

A powerhead that may be utilized by an injector module of an injector system may incorporate at least one syringe plunger driver (e.g., one syringe plunger driver for each syringe that may be installed on the powerhead). The syringe plunger driver may be characterized as a structure that is movable relative to a housing of the powerhead and that may be coupled with a corresponding syringe plunger or piston to move the same relative to its corresponding syringe barrel. Any appropriate drive source (e.g., a motor) may be used to advance a given syringe plunger driver. Representative drive source forms include a brushed or brushless electric motor, a hydraulic motor, a pneumatic motor, a piezoelectric motor, or a stepper motor. A single drive source could be used by the injector module to drive (e.g. separately) one or more syringe plunger drivers (e.g., a common drive source could be used to power multiple syringe plunger drivers). Another option would be for the injector module to have a separate drive source for each syringe plunger driver incorporated by the powerhead. Multiple drive sources could be used to operate a given syringe plunger driver (e.g., a combined power output delivered to a single syringe plunger driver).

An injector module of an injector system may include a base. This base may incorporate what may be characterized as a power pack. Another option is for the power pack to be separate from but in communication with the injector module in any appropriate manner. In any case, the power pack may include an AC/DC converter or an on-board power supply of any appropriate type (e.g., a battery or battery system), a communications module, or any combination thereof. The AC/DC converter may be of any appropriate configuration to convert alternating current to direct current. The communications module may be configured to accommodate at least one-way communications between the injector module and at least one external device (e.g., e.g., an imaging system, a hospital information system (HIS), a contrast media storage/dispensing unit, a radiological information system (RIS), a picture archive and communication system (PACS), a pharmacy information system (PhIS), a hospital management system (HMS), or the like). The communications module may convert data/commands from one format to another format. The communications module may provide conversions between multiple formats to allow the contrast media injector system to communicate with one or more external devices. The power pack may include one or more communication ports to allow the contrast media injector system to communicate with one or more external devices.

A master/slave control architecture may be utilized by the contrast media injector system, where an injector module (e.g., a powerhead) of the injector system is a master node for this control architecture and where each tablet computer and each smart phone used by the injector system is a slave node for this control architecture. A control architecture may be utilized for the contrast media injector system and may be of the type where an injector module (e.g., a powerhead) is a master node and where each tablet computer and each smart phone used by the injector system is a remote node. Although a tablet computer of an injector system may be utilized to accommodate user inputs to the contrast media injector system (including to program an injection protocol, to initiate the execution of an injection protocol, to terminate the execution of an injection protocol, or any combination thereof), the contrast media injector system may be configured to include an injector system control module through which al communications with the drive source(s) must pass, including for the case where a powerhead incorporates this injector system control module. Although a smart phone of an injector system may be utilized to accommodate user inputs to the contrast media injector system (including to program an injection protocol, to initiate the execution of an injection protocol, to terminate the execution of an injection protocol, or any combination thereof), the contrast media injector system may be configured to include an injector system control module through which al communications with the drive source(s) must pass, including for the case where a powerhead incorporates this injector system control module.

An injector module (e.g., a powerhead) of the injector system may have a single stored injection protocol, while at least one tablet computer and/or at least one smart phone of the injector system may store multiple injection protocols. Injection protocols may be stored in any appropriate computer-readable storage medium. An injection protocol may have one or more phases, with each phase including injection parameters such as an amount of fluid to be injected and an injection flow rate, as well as possibly one or more injection delays (sometimes referred to as "holds" and/or "pauses"), and each of which can be of finite or infinite duration. An injection protocol may be characterized as providing for a programmed operation of the contrast media injector system to in relation to the injection of fluid into a patient.

The contrast media injector system may include an injection protocol date structure that includes and/or accommodates a plurality of injection protocols. This injection protocol data structure may be embodied in a computer-readable storage medium of any appropriate type and/or configuration. In one embodiment, the entirety of such an injection protocol data structure is stored on at least one tablet computer of the injector system (e.g., none of the injection protocol data structure is stored on the injector module (e.g., powerhead)). In one embodiment, an entirety of such an injection protocol data structure is stored on at least one smart phone of the injector system (e.g., none of the injection protocol data structure is stored on the injector module (e.g., powerhead)).

The contrast media injector system may include an injection history data structure. Data on injection protocols previously executed by the contrast media injector system may be stored in this injection history data structure. This injection history data structure may be embodied in a computer-readable storage medium of any appropriate type and/or configuration. In one embodiment, the entirety of such an injection history data structure is stored on at least one tablet computer of the injector system (e.g., none of the injection history data structure is stored on the injector module (e.g., a powerhead)). In one embodiment, the entirety of such an injection history data structure is stored on at least one smart phone of the injector system (e.g., none of the injection history data structure is stored on the injector module (e.g., a powerhead)).

The contrast media injector system may include an alarm history data structure. Data on alarms that were generated during injection protocols previously executed by the contrast media injector system may be stored in this alarm history data structure. This alarm history data structure may be embodied in a computer-readable storage medium of any appropriate type and/or configuration. In one embodiment, the entirety of such an alarm history data structure is stored on at least one tablet computer of the injector system (e.g., none of the alarm history data structure is stored on the injector module (e.g., a powerhead)). In one embodiment, the entirety of such an alarm history data structure is stored on at least one smart phone of the injector system (e.g., none of the alarm history data structure is stored on the injector module (e.g., a powerhead)).

The contrast media injector system includes an injector system control module for a given injector module. The contrast media injector system may be configured such that al communications with the drive source(s) are required to pass through this injector system control module. In any case, the contrast media injector system may be configured to require an active communication link between at least one tablet computer of the injector system and the injector system control module before an injection protocol may be executed by the contrast media injector system, the contrast media injector system may be configured to require an active communication link between at least one smart phone of the injector system and the injector system control module before an injection protocol may be executed by the contrast media injector system, or both.

Any tablet computer that is utilized by an injector system may be of any appropriate type, may be of any appropriate configuration, and may use any appropriate operating system. The tablet computer may utilize one or more apps or applications (e.g., stored in memory on the tablet computer), for instance to allow the tablet computer to communicate with and control an injector module (more specifically, its injector system control module) as described herein.

A "tablet computer" as used herein refers to a portable device that does not require a physical keyboard for full operation of the tablet computer (although the tablet computer may include a detachable keyboard and/or be configured (or be configurable) to communicate with an external keyboard, for instance through a USB port or via Bluetooth) (e.g., the tablet computer is fully operable without having a dedicated keyboard attached), that has a display in the form of a touchscreen for providing user input to the computer (e.g., operable by contacting the same with a body part (e.g., one or more fingers), a pen, stylus, or the like), that allows a user to control one or more aspects of an injector system as described herein, and that allows a user to perform one or more of the following functions: a) access, retrieve, read, draft, and/or send email; b) access, retrieve, and/or update a calendar (e.g., modify, delete, and/or add events); c) access, retrieve, and/or update contacts (e.g., modify, delete, and/or add contacts in a contact listing/database); and d) access, browse, search, surf, and/or retrieve information from the Internet. A tablet computer will typically weigh within a range of about 0.5 pounds to about 2.5 pounds. A tablet computer will typically include one or more processors, an operating system (iOS, Android, Windows, Blackberry), memory, a battery, a display (within a range of about 6" to about 11" in one embodiment, measured on the diagonal; within a range of about 5" to about 12" in another embodiment, measured on the diagonal), a Web browser, and a touchscreen. A tablet computer may be Wi-Fi and/or Bluetooth enabled, and may include one or more sensors of any appropriate type to sense the orientation of the tablet computer and which may be used control the orientation that an output is presented on the display (e.g., in either a portrait or landscape orientation).

Any smart phone that is utilized by an injector system may be of any appropriate type, may be of any appropriate configuration, and may use any appropriate operating system. The smart phone may utilize one or more apps or applications (e.g., stored in memory on the smart phone), for instance for allowing the smart phone to communicate with and control an injector module (more specifically, its injector system control module) as described herein. Any appropriate user input device may be utilized by the smart phone, including a touchscreen (e.g., which may present an electronic keyboard; operable by contacting the display with a body part (e.g., one or more fingers), a pen, stylus, or the like), a physical keyboard, or both.

A 'smart phone' as used herein refers to a hand-held device (e.g., where substantially the entirety of the device is containable within a single hand of a user) that allows a user to talk to another individual that is typically at a different location (e.g., using a cellular communication system (e.g., a collection of wireless transmitters); using a microphone and speaker that are incorporated into the structure of the smart phone), that allows a user to control one or more aspects of an injector system as described herein, and that allows a user to perform one or more of the following functions: a) access, retrieve, read, draft, and/or send email; b) access, retrieve, and/or update a calendar (e.g., modify, delete, and/or add events); c) access, retrieve, and/or update contacts (e.g., modify, delete, and/or add contacts in a contact listing/database); and d) access, browse, search, surf, and/or retrieve information from the internet. A smart phone will typically weigh within a range of about 4 ounces to about 6.5 ounces. A smart phone will typically include one or more processors, a mobile computing platform or operating system (iOS, Android, Windows, Blackberry), memory, a battery, a display (typically within a range of about 2" to about 5.5", measured on the diagonal), a Web browser, and a touchscreen (e.g., in the form of the above-noted display, and which may present an electronic keyboard) and/or a physical keyboard (e.g., with a separate depressable button or key for each letter of the alphabet, such as a Qwerty keyboard). A smart phone may be Wi-Fi and/or Bluetooth enabled, and may include one or more sensors of any appropriate type to sense the orientation of the smart phone and which may be used control the orientation that an output is presented on the display (e.g., in either a portrait or landscape orientation).

A user could carry a smart phone of an injector system and use the same to control one or more aspects of the operation of an injector module, for instance to program an injection protocol, to initiate the execution of an injection protocol, to terminate the execution of an injection protocol, or any combination thereof. The smart phone could also be incorporated by an appropriate carrier (e.g., in accordance with the user-mountable user input device discussed above; so as to be "mountable" on a user, including where the user may operate the smart phone while appropriately mounted to the user). Injection results of any appropriate type may be displayed on a smart phone (e.g., on a display, which may be in the form of a touchscreen).

The injector systems described herein may be utilized and/or adapted in any appropriate manner for multi-dosing/multi-patient applications (e.g., injector systems that use a bulk supply of at least one contrast media to accommodate multiple executions of one or more injection protocols, typically to different patients). For instance, the injector systems could use a multi-patient tubing set (used for multiple patients) that is detachably connected to a patient-specific or disposable tubing set (a patient-specific tubing set being used for only one patient). Multi-dosing/multi-patient injector system configurations of any appropriate type may be utilized.

The injector systems described herein may be used for any appropriate application where the delivery of one or more medical fluids is desired, including without limitation any appropriate medical application (e.g., computed tomography or CT imaging; magnetic resonance imaging or MRI; single photon emission computed tomography or SPECT imaging; positron emission tomography or PET imaging; X-ray imaging; angiographic imaging; optical imaging; ultrasound imaging). Any such injector system may be used in conjunction with any component or combination of components, such as an appropriate imaging system (e.g., a CT scanner). For instance, information could be conveyed between one or more injector modules and one or more other components (e.g., scan delay information, injection start signal, injection rate).

Any syringe plunger driver used by a power injector of any injector system described herein may be of any appropriate size, shape, configuration, and/or type, where each such syringe plunger driver may be capable of at least bi-directional movement (e.g., a movement in a first direction for discharging fluid; a movement in a second direction for accommodating a loading and/or drawing of fluid and/or so as to return to a position for a subsequent fluid discharge operation), and where each such syringe plunger driver may interact with its corresponding syringe plunger in any appropriate manner (e.g., by mechanical contact; by an appropriate coupling (mechanical or otherwise)) so as to be able to advance the syringe plunger in at least one direction (e.g., to discharge fluid). Each syringe plunger driver may utilize one or more drive sources of any appropriate size, shape, configuration, and/or type. Multiple drive source outputs may be combined in any appropriate manner to advance a single syringe plunger at a given time. One or more drive sources may be dedicated to a single syringe plunger driver, one or more drive sources may be associated with multiple syringe plunger drivers (e.g., incorporating a transmission of sorts to change the output from one syringe plunger to another syringe plunger), or a combination thereof. Representative drive source forms include a brushed or brushless electric motor, a hydraulic motor, a pneumatic motor, a piezoelectric motor, or a stepper motor.

One or more syringes may be installed in any appropriate manner (e.g., detachably; front-loaded; rear-loaded; side-loaded) on a powerhead used by any injector system described herein, any appropriate medical fluid may be discharged from a given syringe of the power injector (e.g., contrast media, a radiopharmaceutical, saline, and any combination thereof) on any power injector used by any injector system described herein, any appropriate fluid may be discharged from a multiple syringe power injector configuration in any appropriate manner (e.g., sequentially, simultaneously), or any combination thereof. In one embodiment, fluid discharged from a syringe by operation of a power injector of an injector system is directed into a conduit (e.g., medical tubing set), where this conduit is fluidly interconnected with the syringe in any appropriate manner and directs fluid to a desired location (e.g., to a catheter that is inserted into a patient for injection). Multiple syringes may discharge into a common conduit (e.g., for provision to a single injection site), or one syringe may discharge into one conduit (e.g., for provision to one injection site), while another syringe may discharge into a different conduit (e.g., for provision to a different injection site). In one embodiment, each syringe includes a syringe barrel and a plunger that is disposed within and movable relative to the syringe barrel. This plunger may interface with the power injector's syringe plunger drive assembly such that the syringe plunger drive assembly is able to advance the plunger in at least one direction, and possibly in two different, opposite directions.

Any feature of the present invention that is intended to be limited to a "singular" context or the like will be clearly set forth herein by terms such as "only," "single," "limited to," or the like. Merely introducing a feature in accordance with commonly accepted antecedent basis practice does not limit the corresponding feature to the singular (e.g., indicating that a power injector includes "a syringe" alone does not mean that the power injector includes only a single syringe).

Moreover, any failure to use phrases such as 'at least one' also does not limit the corresponding feature to the singular (e.g., indicating that a power injector includes "a syringe" alone does not mean that the power injector includes only a single syringe). Finally, use of the phrase "at least generally" or the like in relation to a particular feature encompasses the corresponding characteristic and insubstantial variations thereof (e.g., indicating that a syringe barrel is at least generally cylindrical encompasses the syringe barrel actually being cylindrical).

BRIEF DESCRIPTION OF THE FIGURES

FIG. 6A is a block diagram of one embodiment a contrast media injector system where a tablet computer may be docked to an injector module of one configuration.

FIG. 6B is a block diagram of another embodiment a contrast media injector system where a tablet computer may be docked to an injector module of another configuration.

DETAILED DESCRIPTION

Figure 1:
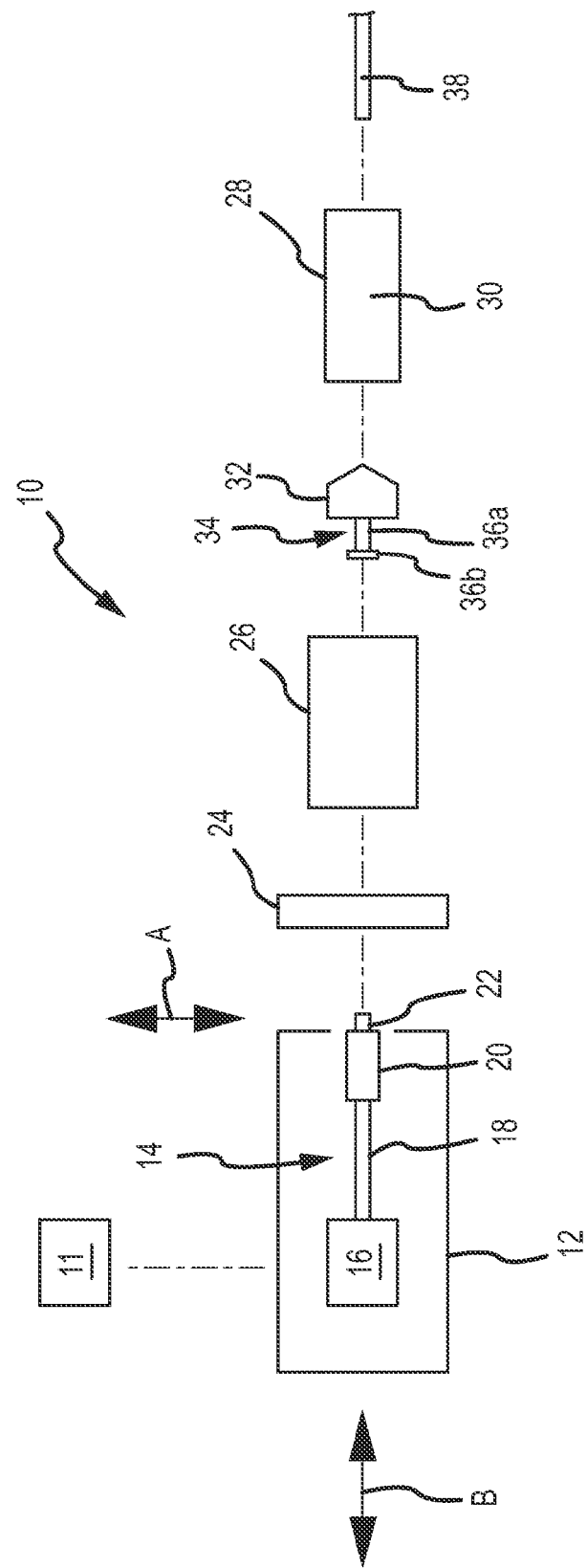
FIG. 1 is a schematic of one embodiment of a power injector.

FIG. 1 presents a schematic of one embodiment of an injector module or power injector 10 having a powerhead 12. One or more graphical user interfaces or GUIs 11 may be associated with the powerhead 12. Each GUI 11: 1) may be of any appropriate size, shape, configuration, and/or type; 2) may be operatively interconnected with the powerhead 12 in any appropriate manner; 3) may be disposed at any appropriate location; 4) may be configured to provide any of the following functions: controlling one or more aspects of the operation of the power injector 10; inputting/editing one or more parameters associated with the operation of the power injector 10; and displaying appropriate information (e.g., associated with the operation of the power injector 10); or 5) any combination of the foregoing. Any appropriate number of GUIs 11 may be utilized. In one embodiment, the power injector 10 includes a GUI 11 that is incorporated by a console that is separate from but which communicates with the powerhead 12. In another embodiment, the power injector 10 includes a GUI 11 that is part of the powerhead 12. In yet another embodiment, the power injector 10 utilizes one GUI 11 on a separate console that communicates with the powerhead 12, and also utilizes another GUI 11 that is on the powerhead 12. Each GUI 11 could provide the same functionality or set of functionalities, or the GUIs 11 may differ in at least some respect in relation to their respective functionalities.

A syringe 28 may be installed on the powerhead 12 and, when installed, may be considered to be part of the power injector 10. Some injection procedures may result in a relatively high pressure being generated within the syringe 28. In this regard, it may be desirable to dispose the syringe 28 within a pressure jacket 26. The pressure jacket 26 is typically associated with the powerhead 12 in a manner that allows the syringe 28 to be disposed therein as a part of or after installing the syringe 28 on the powerhead 12. The same pressure jacket 26 will typically remain associated with the powerhead 12, as various syringes 28 are positioned within and removed from the pressure jacket 26 for multiple injection procedures. The power injector 10 may eliminate the pressure jacket 26 if the power injector 10 is configured/utilized for low-pressure injections and/or if the syringe(s) 28 to be utilized with the power injector 10 is (are) of sufficient durability to withstand high-pressure injections without the additional support provided by a pressure jacket 26. In any case, fluid discharged from the syringe 28 may be directed into a conduit 38 of any appropriate size, shape, configuration, and/or type, which may be fluidly interconnected with the syringe 28 in any appropriate manner, and which may direct fluid to any appropriate location (e.g., to a patient).

The powerhead 12 includes a syringe plunger drive assembly or syringe plunger driver 14 that interacts (e.g., interfaces) with the syringe 28 (e.g., a plunger 32 thereof) to discharge fluid from the syringe 28. This syringe plunger drive assembly 14 includes a drive source 16 (e.g., a motor of any appropriate size, shape, configuration, and/or type, optional gearing, and the like) that powers a drive output 18 (e.g., a rotatable drive screw). A ram 20 may be advanced along an appropriate path (e.g., axial) by the drive output 18. The ram 20 may include a coupler 22 for interacting or interfacing with a corresponding portion of the syringe 28 in a manner that will be discussed below.

The syringe 28 includes a plunger or piston 32 that is movably disposed within a syringe barrel 30 (e.g., for axial reciprocation along an axis coinciding with the double-headed arrow B). The plunger 32 may include a coupler 34. This syringe plunger coupler 34 may interact or interface with the ram coupler 22 to allow the syringe plunger drive assembly 14 to retract the syringe plunger 32 within the syringe barrel 30. The syringe plunger coupler 34 may be in the form of a shaft 36a that extends from a body of the syringe plunger 32, together with a head or button 36b. However, the syringe plunger coupler 34 may be of any appropriate size, shape, configuration, and/or type.

Generally, the syringe plunger drive assembly 14 of the power injector 10 may interact with the syringe plunger 32 of the syringe 28 in any appropriate manner (e.g., by mechanical contact; by an appropriate coupling (mechanical or otherwise)) so as to be able to move or advance the syringe plunger 32 (relative to the syringe barrel 30) in at least one direction (e.g., to discharge fluid from the corresponding syringe 28). That is, although the syringe plunger drive assembly 14 may be capable of bi-directional motion (e.g., via operation of the same drive source 16), the power injector 10 may be configured such that the operation of the syringe plunger drive assembly 14 actually only moves each syringe plunger 32 being used by the power injector 10 in only one direction. However, the syringe plunger drive assembly 14 may be configured to interact with each syringe plunger 32 being used by the power injector 10 so as to be able to move each such syringe plunger 32 in each of two different directions (e.g. in different directions along a common axial path).

Retraction of the syringe plunger 32 may be utilized to accommodate a loading of fluid into the syringe barrel 30 for a subsequent-injection or discharge, may be utilized to actually draw fluid into the syringe barrel 30 for a subsequent injection or discharge, or for any other appropriate purpose. Certain configurations may not require that the syringe plunger drive assembly 14 be able to retract the syringe plunger 32, in which case the ram coupler 22 and syringe plunger coupler 34 may not be desired. In this case, the syringe plunger drive assembly 14 may be retracted for purposes of executing another fluid delivery operation (e.g., after another pre-filed syringe 28 has been installed). Even when a ram coupler 22 and syringe plunger coupler 34 are utilized, these components may or may not be coupled when the ram 20 advances the syringe plunger 32 to discharge fluid from the syringe 28 (e.g., the ram 20 may simply "push on" the syringe plunger coupler 34 or directly on a proximal end of the syringe plunger 32). Any single motion or combination of motions in any appropriate dimension or combination of dimensions may be utilized to dispose the ram coupler 22 and syringe plunger coupler 34 in a coupled state or condition, to dispose the ram coupler 22 and syringe plunger coupler 34 in an un-coupled state or condition, or both.

The syringe 28 may be installed on the powerhead 12 in any appropriate manner. For instance, the syringe 28 could be configured to be installed directly on the powerhead 12. In the illustrated embodiment, a housing 24 is appropriately mounted on the powerhead 12 to provide an interface between the syringe 28 and the powerhead 12. This housing 24 may be in the form of an adapter to which one or more configurations of syringes 28 may be installed, and where at least one configuration for a syringe 28 could be installed directly on the powerhead 12 without using any such adapter. The housing 24 may also be in the form of a faceplate to which one or more configurations of syringes 28 may be installed. In this case, it may be such that a faceplate is required to install a syringe 28 on the powerhead 12—the syringe 28 could not be installed on the powerhead 12 without the faceplate. When a pressure jacket 26 is being used, it may be installed on the powerhead 12 in the various manners discussed herein in relation to the syringe 28, and the syringe 28 will then thereafter be installed in the pressure jacket 26.

The housing 24 may be mounted on and remain in a fixed position relative to the powerhead 12 when installing a syringe 28. Another option is to movably interconnect the housing 24 and the powerhead 12 to accommodate installing a syringe 28. For instance, the housing 24 may move within a plane that contains the double-headed arrow A to provide one or more of coupled state or condition and an un-coupled state or condition between the ram coupler 22 and the syringe plunger coupler 34.

Figure 2A:
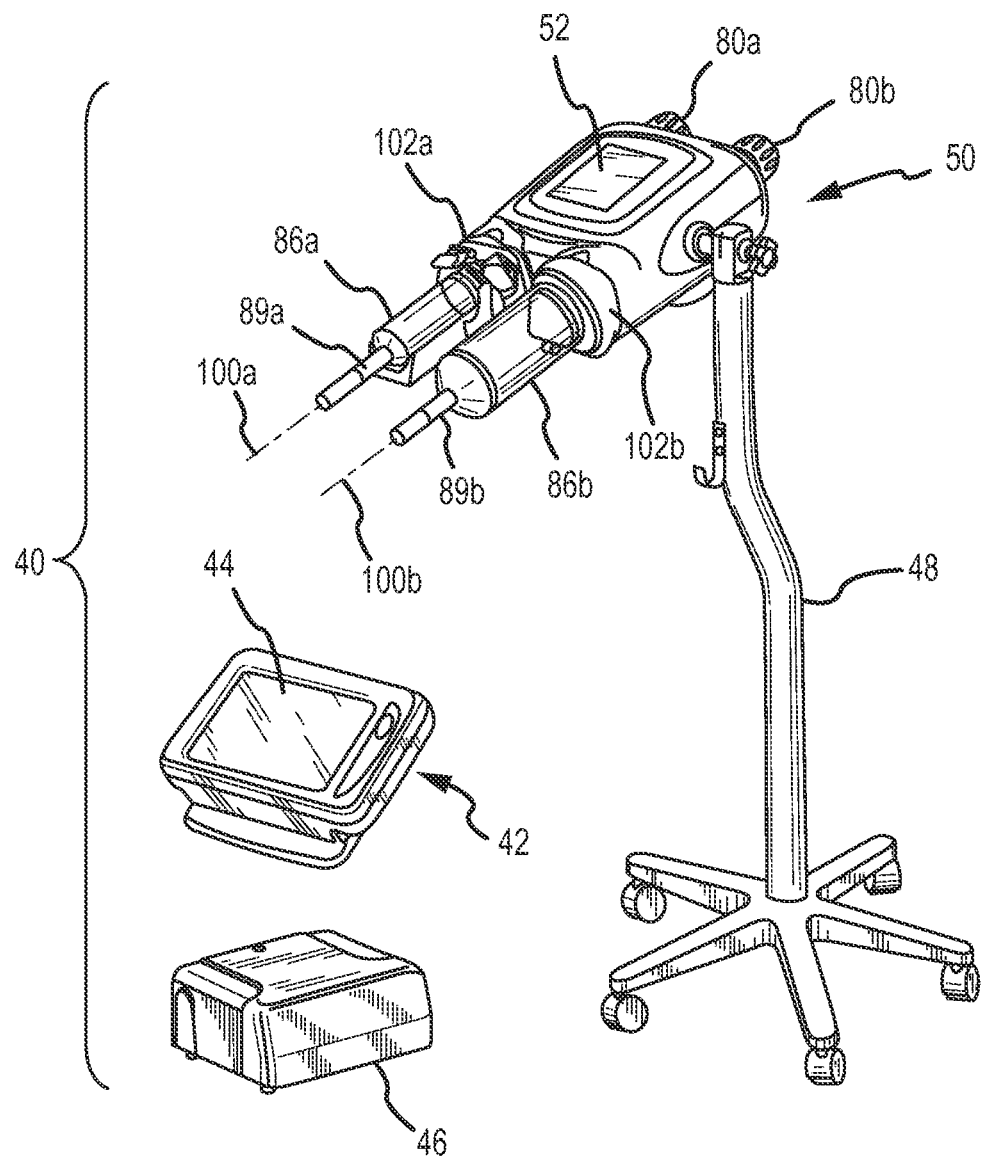
FIG. 2A is a perspective view of one embodiment of a portable stand-mounted, dual-head power injector.

One particular power injector configuration is illustrated in FIG. 2A, is identified by a reference numeral 40, and is at least generally in accordance with the power injector 10 of FIG. 1. The power injector 40 includes a powerhead 50 that is mounted on a portable stand 48. The powerhead 50 and stand 48 may be collectively referred to as an injector module. Two syringes 86a, 86b for the power injector 40 are mounted on the powerhead 50. Fluid may be discharged from the syringes 86a, 86b during operation of the power injector 40.

The portable stand 48 may be of any appropriate size, shape, configuration, and/or type. Wheels, rollers, casters, or the like may be utilized to make the stand 48 portable. The powerhead 50 could be maintained in a fixed position relative to the portable stand 48. However, it may be desirable to allow the position of the powerhead 50 to be adjustable relative to the portable stand 48 in at least some manner. For instance, it may be desirable to have the powerhead 50 in one position relative to the portable stand 48 when loading fluid into one or more of the syringes 86a, 86b, and to have the powerhead 50 in a different position relative to the portable stand 48 for performance of an injection procedure. In this regard, the powerhead 50 may be movably interconnected with the portable stand 48 in any appropriate manner (e.g., such that the powerhead 50 may be pivoted through at least a certain range of motion, and thereafter maintained in the desired position).

It should be appreciated that the powerhead 50 could be supported in any appropriate manner for providing fluid. For instance, instead of being mounted on a portable structure, the powerhead 50 could be interconnected with a support assembly, that in turn is mounted to an appropriate structure (e.g., ceiling, wall, floor). Any support assembly for the powerhead 50 may be positionally adjustable in at least some respect (e.g., by having one or more support sections that may be repositioned relative to one or more other support sections), or may be maintained in a fixed position. Moreover, the powerhead 50 may be integrated with any such support assembly so as to either be maintained in a fixed position or so as to be adjustable relative the support assembly.

The powerhead 50 includes a graphical user interface or GUI 52. This GUI 52 may be configured to provide one or any combination of the following functions: controlling one or more aspects of the operation of the power injector 40; inputting/editing one or more parameters associated with the operation of the power injector 40; and displaying appropriate information (e.g., associated with the operation of the power injector 40). The power injector 40 may also include a console 42 and powerpack 46 that each may be in communication with the powerhead 50 in any appropriate manner (e.g., via one or more cables), that may be placed on a table or mounted on an electronics rack in an examination room or at any other appropriate location, or both. The powerpack 46 may include one or more of the following and in any appropriate combination: a power supply for the injector 40; interface circuitry for providing communication between the console 42 and powerhead 50; circuitry for permitting connection of the power injector 40 to remote units such as remote consoles, remote hand or foot control switches, or other original equipment manufacturer (OEM) remote control connections (e.g., to allow for the operation of power injector 40 to be synchronized with the x-ray exposure of an imaging system); and any other appropriate componentry. The console 42 may include a touch screen display 44, which in turn may provide one or more of the following functions and in any appropriate combination: allowing an operator to remotely control one or more aspects of the operation of the power injector 40; allowing an operator to enter/edit one or more parameters associated with the operation of the power injector 40; allowing an operator to specify and store programs for automated operation of the power injector 40 (which can later be automatically executed by the power injector 40 upon initiation by the operator); and displaying any appropriate information relation to the power injector 40 and including any aspect of its operation. In the illustrated embodiment, the powerpack 46 and remote console 42 would not be considered as part of the injector module (again, where this injector module is in the form of the powerhead 50 and stand 48).

Figure 2B:
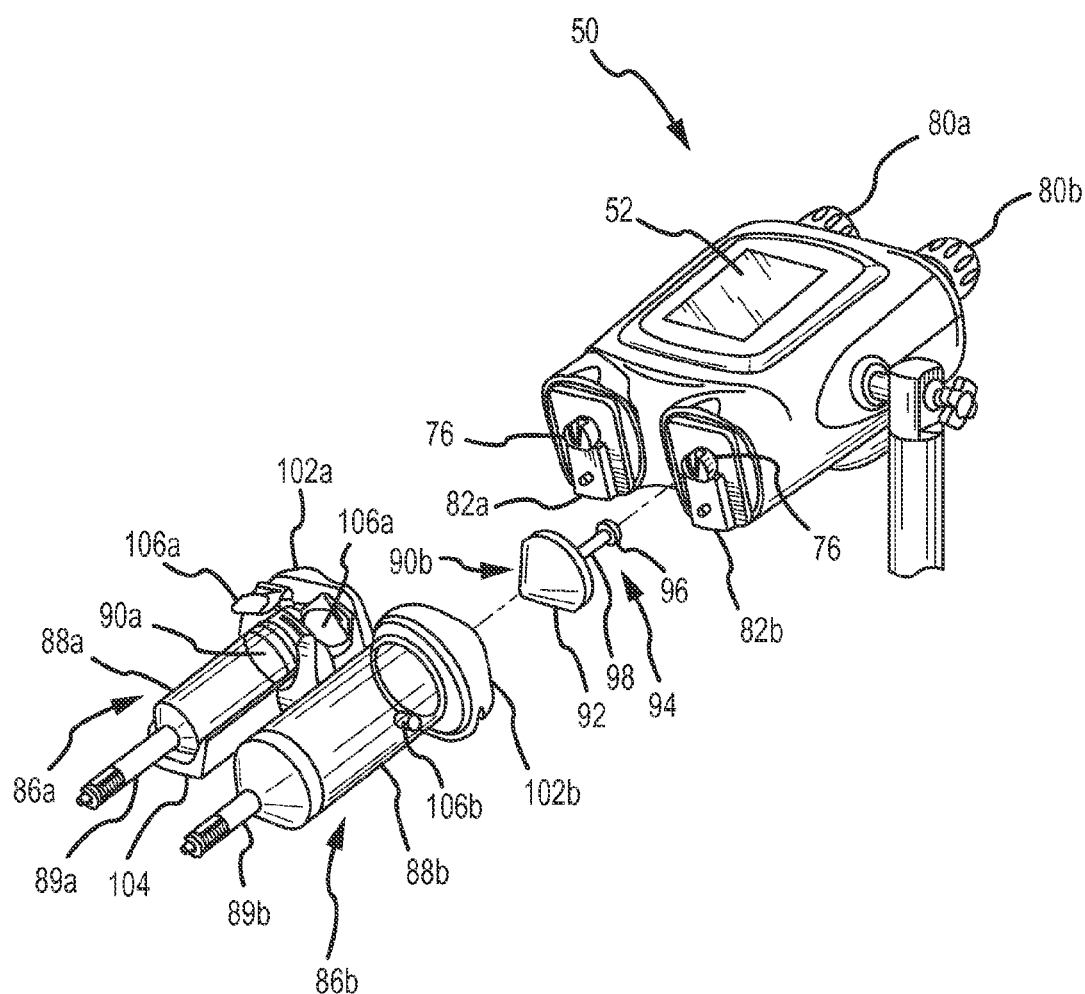
FIG. 2B is an enlarged, partially exploded, perspective view of a powerhead used by the power injector of FIG. 2A.

Various details regarding the integration of the syringes 86a, 86b with the powerhead 50 are presented in FIG. 2B. Each of the syringes 86a, 86b includes the same general components. The syringe 86a includes plunger or piston 90a that is movably disposed within a syringe barrel 88a. Movement of the plunger 90a along an axis 100a (FIG. 2A) via operation of the powerhead 50 will discharge fluid from within a syringe barrel 88a through a nozzle 89a of the syringe 86a. An appropriate conduit (not shown) will typically be fluidly interconnected with the nozzle 89a in any appropriate manner to direct fluid to a desired location (e.g., a patient). Similarly, the syringe 86b includes plunger or piston 90b that is movably disposed within a syringe barrel 88b. Movement of the plunger 90b along an axis 100b (FIG. 2A) via operation of the powerhead 50 will discharge fluid from within the syringe barrel 88b through a nozzle 89b of the syringe 86b. An appropriate conduit (not shown) will typically be fluidly interconnected with the nozzle 89b in any appropriate manner to direct fluid to a desired location (e.g., a patient).

The syringe 86a is interconnected with the powerhead 50 via an intermediate faceplate 102a. This faceplate 102a includes a cradle 104 that supports at least part of the syringe barrel 88a, and which may provide/accommodate any additional functionality or combination of functionalities. A mounting 82a is disposed on and is fixed relative to the powerhead 50 for interfacing with the faceplate 102a. A ram coupler 76 of a ram 74 (FIG. 20), which are each part of a syringe plunger drive assembly or syringe plunger driver 56 (FIG. 20) for the syringe 86a, is positioned in proximity to the faceplate 102a when mounted on the powerhead 50. Details regarding the syringe plunger drive assembly 56 will be discussed in more detail below in relation to FIG. 2C.

Generally, the ram coupler 76 may be coupled with the syringe plunger 90a of the syringe 86a, and the ram coupler 76 and ram 74 (FIG. 2C) may then be moved relative to the powerhead 50 to move the syringe plunger 90a along the axis 100a (FIG. 2A). It may be such that the ram coupler 76 is engaged with, but not actually coupled to, the syringe plunger 90a when moving the syringe plunger 90a to discharge fluid through the nozzle 89a of the syringe 86a.

The faceplate 102a may be moved at least generally within a plane that is orthogonal to the axes 100a, 100b (associated with movement of the syringe plungers 90a, 90b, respectively, and illustrated in FIG. 2A), both to mount the faceplate 102a on and remove the faceplate 102a from its mounting 82a on the powerhead 50. The faceplate 102a may be used to couple the syringe plunger 90a with its corresponding ram coupler 76 on the powerhead 50. In this regard, the faceplate 102a includes a pair of handles 106a. Generally and with the syringe 86a being initially positioned within the faceplate 102a, the handles 106a may be moved to in turn move/translate the syringe 868 at least generally within a plane that is orthogonal to the axes 100a, 100b (associated with movement of the syringe plungers 90a, 90b, respectively, and illustrated in FIG. 2A). Moving the handles 106a to one position moves/translates the syringe 86a (relative to the faceplate 102a) in an at least generally downward direction to couple its syringe plunger 90a with its corresponding ram coupler 76. Moving the handles 106a to another position moves/translates the syringe 86a (relative to the faceplate 102a) in an at least generally upward direction to uncouple its syringe plunger 90a from its corresponding ram coupler 76.

The syringe 86b is interconnected with the powerhead 50 via an intermediate faceplate 102b. A mounting 82b is disposed on and is fixed relative to the powerhead 50 for interfacing with the faceplate 102b. A ram coupler 76 of a ram 74 (FIG. 2C), which are each part of a syringe plunger drive assembly 56 for the syringe 86b, is positioned in proximity to the faceplate 102b when mounted to the powerhead 50. Details regarding the syringe plunger drive assembly 56 again will be discussed in more detail below in relation to FIG. 2C. Generally, the ram coupler 76 may be coupled with the syringe plunger 90b of the syringe 86b, and the ram coupler 76 and ram 74 (FIG. 2C) may be moved relative to the powerhead 50 to move the syringe plunger 90b along the axis 100b (FIG. 2A). It may be such that the ram coupler 76 is engaged with, but not actually coupled to, the syringe plunger 90b when moving the syringe plunger 90b to discharge fluid through the nozzle 89b of the syringe 86b.

The faceplate 102b may be moved at least generally within a plane that is orthogonal to the axes 100a, 100b (associated with movement of the syringe plungers 90a, 90b, respectively, and illustrated in FIG. 2A), both to mount the faceplate 102b on and remove the faceplate 102b from its mounting 82b on the powerhead 50. The faceplate 102b also may be used to couple the syringe plunger 90b with its corresponding ram coupler 76 on the powerhead 50. In this regard, the faceplate 102b may include a handle 106b. Generally and with the syringe 86b being initially positioned within the faceplate 102b, the syringe 86b may be rotated along its long axis 100b (FIG. 2A) and relative to the faceplate 102b. This rotation may be realized by moving the handle 106b, by grasping and turning the syringe 86b, or both. In any case, this rotation moves/translates both the syringe 86b and the faceplate 102b at least generally within a plane that is orthogonal to the axes 100a, 100b (associated with movement of the syringe plungers 90a, 90b, respectively, and illustrated in FIG. 2A). Rotating the syringe 86*b* in one direction moves/translates the syringe 86*b* and faceplate 102*b* in an at least generally downward direction to couple the syringe plunger 90*b* with its corresponding ram coupler 76. Rotating the syringe 86*b* in the opposite direction moves/translates the syringe 86*b* and faceplate 102*b* in an at least generally upward direction to uncouple its syringe plunger 90*b* from its corresponding ram coupler 76.

As illustrated in FIG. 2B, the syringe plunger 90*b* includes a plunger body 92 and a syringe plunger coupler 94. This syringe plunger coupler 94 includes a shat 98 that extends from the plunger body 92, along with a head 96 that is spaced from the plunger body 92. Each of the ram couplers 76 includes a larger slot that is positioned behind a smaller slot on the face of the ram coupler 76. The head 96 of the syringe plunger coupler 94 may be positioned within the larger slot of the ram coupler 76, and the shaft 96 of the syringe plunger coupler 94 may extend through the smaller slot on the face of the ram coupler 76 when the syringe plunger 90*b* and its corresponding ram coupler 76 are in a coupled state or condition. The syringe plunger 90*a* may include a similar syringe plunger coupler 94 for interfacing with its corresponding ram coupler 76.

Figure 2C:
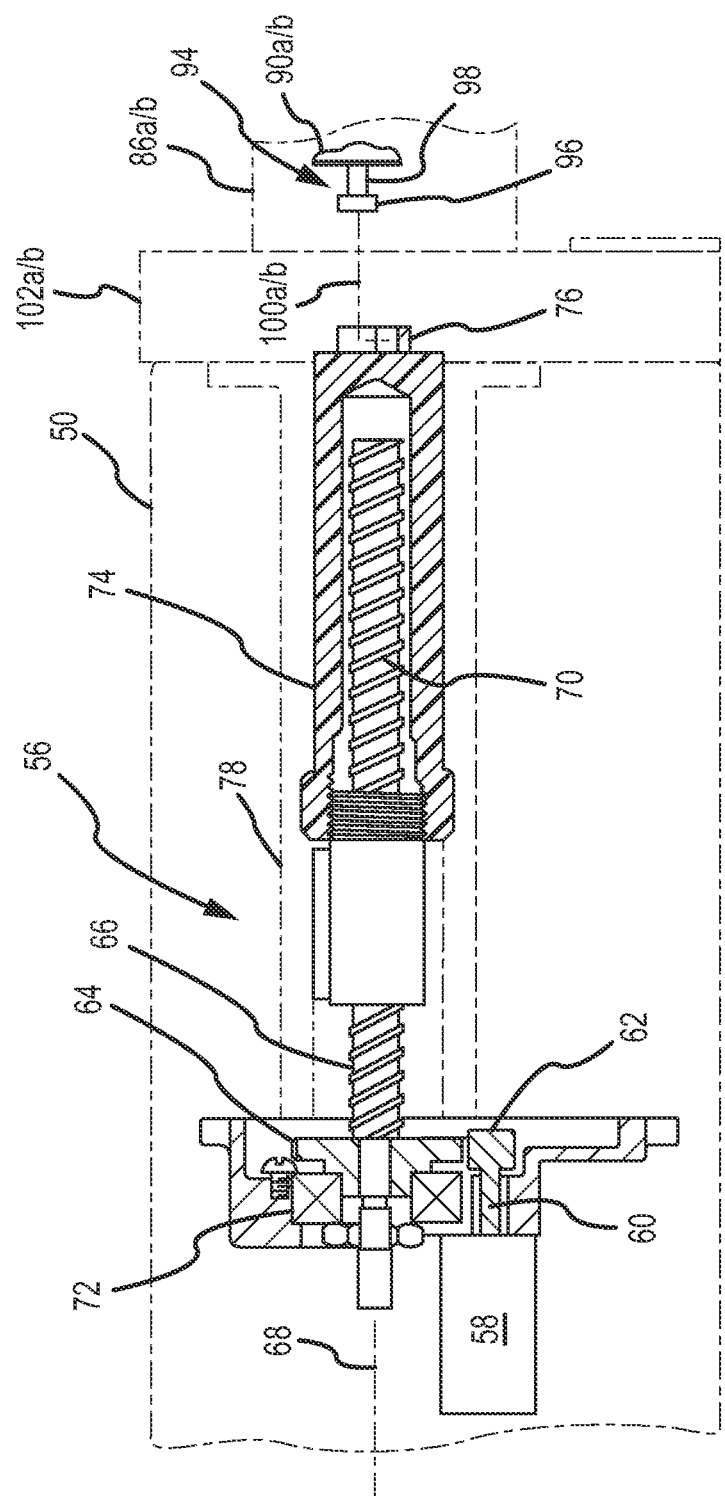
FIG. 2C is a schematic of one embodiment of a syringe plunger drive assembly used by the power injector of FIG. 2A.

The powerhead 50 is utilized to discharge fluid from the syringes 86*a*, 86*b* in the case of the power injector 40. That is, the powerhead 50 provides the motive force to discharge fluid from each of the syringes 86*a*, 86*b*. One embodiment of what may be characterized as a syringe plunger drive assembly or syringe plunger driver is illustrated in FIG. 2C, is identified by reference numeral 56, and may be utilized by the powerhead 50 to discharge fluid from each of the syringes 86*a*, 86*b*. A separate syringe plunger drive assembly 56 may be incorporated into the powerhead 50 for each of the syringes 86*a*, 86*b*. In this regard and referring back to FIGS. 2A-B, the powerhead 50 may include hand-operated knobs 80*a* and 80*b* for use in separately controlling each of the syringe plunger drive assemblies 56.

Initially and in relation to the syringe plunger drive assembly 56 of FIG. 2C, each of its individual components may be of any appropriate size, shape, configuration and/or type. The syringe plunger drive assembly 56 includes a motor 58, which has an output shaft 60. A drive gear 62 is mounted on and rotates with the output shaft 60 of the motor 58. The drive gear 62 is engaged or is at least engageable with a driven gear 64. This driven gear 64 is mounted on and rotates with a drive screw or shalt 66. The axis about which the drive screw 66 rotates is identified by reference numeral 68. One or more bearings 72 appropriately support the drive screw 66.

A carriage or ram 74 is movably mounted on the drive screw 66. Generally, rotation of the drive screw 66 in one direction axially advances the ram 74 along the drive screw 66 (and thereby along axis 68) in the direction of the corresponding syringe 86*a/b*, while rotation of the drive screw 66 in the opposite direction axially advances the ram 74 along the drive screw 66 (and thereby along axis 68) away from the corresponding syringe 86*a/b*. In this regard, the perimeter of at least part of the drive screw 66 includes helical threads 70 that interface with at least part of the ram 74. The ram 74 is also movably mounted within an appropriate bushing 78 that does not allow the ram 74 to rotate during a rotation of the drive screw 66. Therefore, the rotation of the drive screw 66 provides for an axial movement of the ram 74 in a direction determined by the rotational direction of the drive screw 66.

The ram 74 includes a coupler 76 that that may be detachably coupled with a syringe plunger coupler 94 of the syringe plunger 90*a/b* of the corresponding syringe 86*a/b*. When the ram coupler 76 and syringe plunger coupler 94 are appropriately coupled, the syringe plunger 90*a/b* moves along with ram 74. FIG. 2C illustrates a configuration where the syringe 86*a/b* may be moved along its corresponding axis 100*a/b* without being coupled to the ram 74. When the syringe 86*a/b* is moved along its corresponding axis 100*a/b* such that the head 96 of its syringe plunger 90*a/b* is aligned with the ram coupler 76, but with the axes 68 still in the offset configuration of FIG. 2C, the syringe 86*a/b* may be translated within a plane that is orthogonal to the axis 68 along which the ram 74 moves. This establishes a coupled engagement between the ram coupler 76 and the syringe plunger coupler 96 in the above-noted manner.

The power injectors 10, 40 of FIGS. 1 and 2A-C each may be used for any appropriate application, including without limitation for medical imaging applications where fluid is injected into a subject (e.g., a patient) and/or any appropriate medical diagnostic and/or therapeutic application (e.g., injection of chemotherapy, pain management, etc.). Representative medical imaging applications for the power injectors 10, 40 include without limitation computed tomography or CT imaging, magnetic resonance imaging or MRI, single photon emission computed tomography or SPECT imaging, positron emission tomography or PET imaging, X-ray imaging, angiographic imaging, optical imaging, and ultrasound imaging. The power injectors 10, 40 each could be used alone or in combination with one or more other components. The power injectors 10, 40 each may be operatively interconnected with one or more components, for instance so that information may be conveyed between the power injector 10, 40 and one or more other components (e.g., scan delay information, injection start signal, injection rate).

Any number of syringes may be utilized by each of the power injectors 10, 40, including without limitation single-head configurations (for a single syringe) and dual-head configurations (for two syringes). In the case of a multiple syringe configuration, each power injector 10, 40 may discharge fluid from the various syringes in any appropriate manner and according to any timing sequence (e.g., sequential discharges from two or more syringes, simultaneous discharges from two or more syringes, or any combination thereof). Multiple syringes may discharge into a common conduit (e.g., for provision to a single injection site), or one syringe may discharge into one conduit (e.g., for provision to one injection site), while another syringe may discharge into a different conduit (e.g., for provision to a different injection site). Each such syringe utilized by each of the power injectors 10, 40 may include any appropriate fluid (e.g., a medical fluid), for instance contrast media, therapeutic fluid, a radiopharmaceutical, saline, and any combination thereof. Each such syringe utilized by each of the power injectors 10, 40 may be installed in any appropriate manner (e.g., rear-loading configurations may be utilized; front-loading configurations may be utilized; side-loading configurations may be utilized).

Figure 3A:
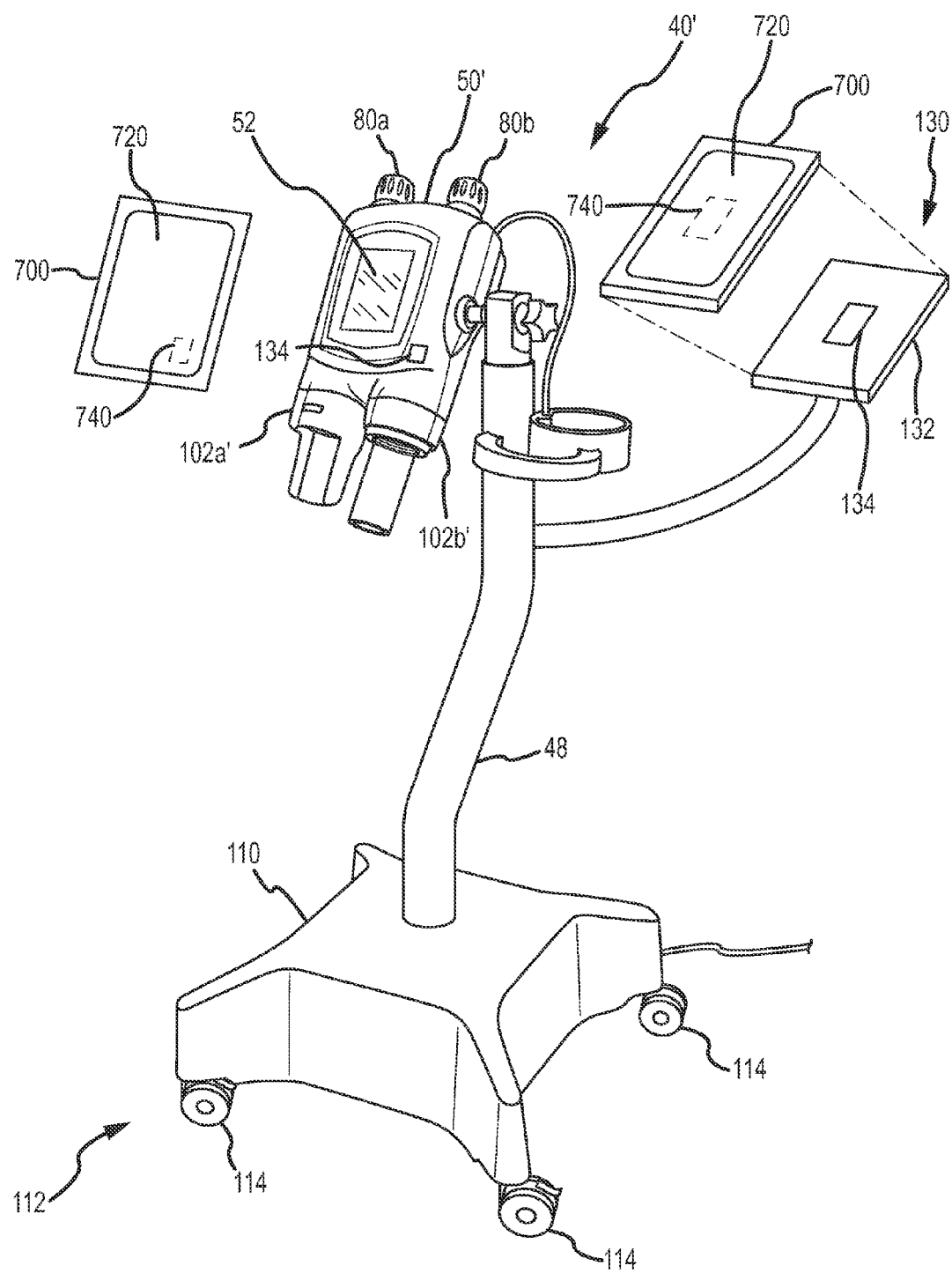
FIG. 3A is a perspective view of one embodiment of a contrast media injector system having a powerhead of a dual-head configuration, and illustrating two different options for incorporating a tablet computer docking station.
Figure 3B:
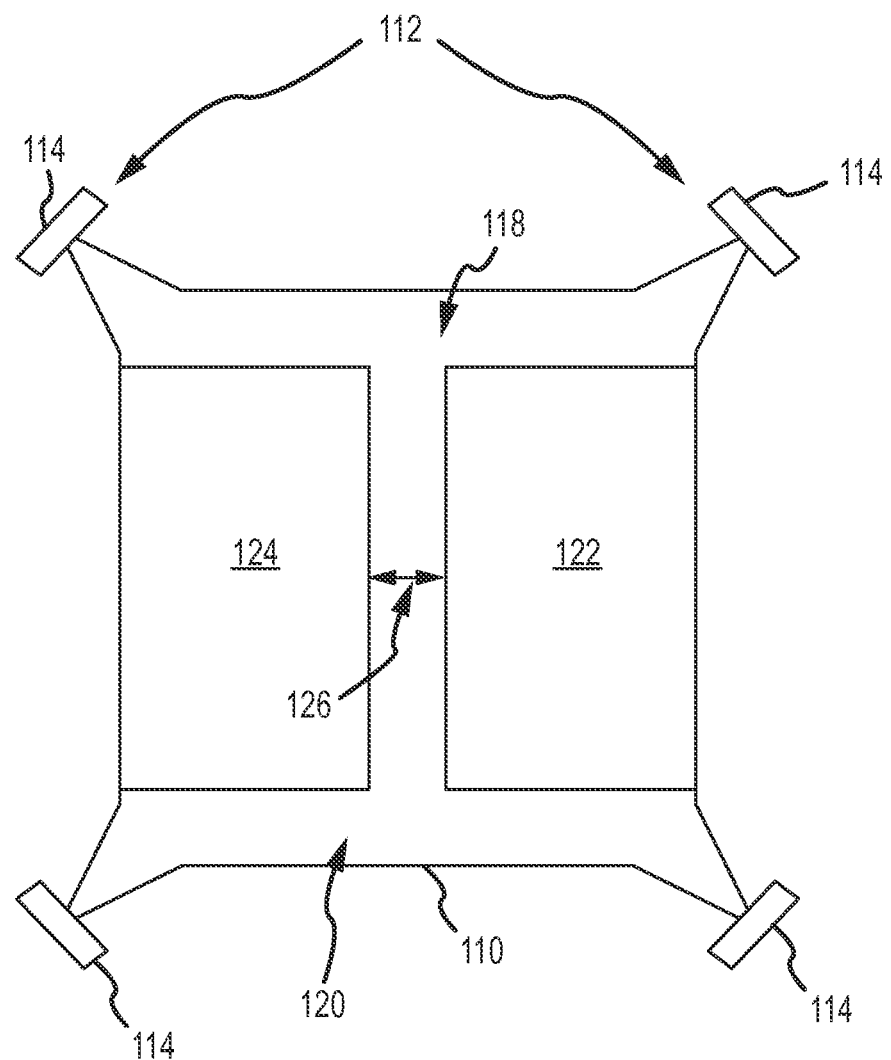
FIG. 3B is a bottom view of a base of the contrast media injector system of FIG. 4A, illustrating a power pack that is incorporated within an interior cavity of the base for the injector system.

One embodiment of a contrast media injector system in the form of a power injector is illustrated in FIGS. 3A and 3B, is identified by a reference numeral 40', and is a variation of the power injector 40 of FIGS. 2A-C. Corresponding components between the power injector 40 of FIGS. 2A-C and the power injector 40' of FIGS. 3A-B are identified by the same reference numerals. Those corresponding components that differ in at least some respect are identified by a "single prime" designation in FIGS. 3A-B. Although only certain of the components are identified by a reference numeral in FIGS. 3A-B, the power injector 40' may in fact utilize all of the features discussed above in relation to the power injector 40 of FIGS. 2A-C that pertain to a dual head power injector, unless otherwise noted.

A key difference between the power injector 40 of FIGS. 2A-C and the power injector 40' of FIGS. 3A-B is that the power injector 40' accommodates connection of a tablet computer 700 thereto. The tablet computer 700 includes a touchscreen 720—a device that accepts user input through contact with the touchscreen 720. The graphical user interface 52 on the powerhead 50' could also be in the form of a touchscreen (e.g., at least two user input devices may be available to provide data inputs to the power injector 40'). In any case, the tablet computer 700 may include at least one docking connector or port 740. This docking connector or port 740 may allow the tablet computer 700 to draw power from the power injector 40' when the tablet computer 700 is docked to the power injector 40'. Although a docking connector or port 740 could be incorporated by the tablet computer 700 to provide for data communication between the tablet computer 700 and the power injector 40', this may not be required if the tablet computer 700 is able to communicate wirelessly with the power injector 40' and as will be addressed below.

The tablet computer 700 may be used in the operation of the power injector 40'. In one embodiment, the tablet computer 700 may be characterized as a replacement for a remote console (e.g., a desktop computer that may be located in a different room than the power injector) that is typically used in conjunction with power injectors. In one embodiment, the tablet computer 700 need not be docked to the power injector 40' in order for the tablet computer 700 to be used in conjunction with the operation of the power injector 40'. In this case both the graphical user interface 52 on the powerhead 50' and the tablet computer 700 would be available to accept user input. The power injector 40' could be configured to require an active communication link between the tablet computer 700 and the power injector 40' in order for the power injector 40' to be fully operational (e.g., the power injector 40' could poll the tablet computer 700, and if the tablet computer 700 did not respond, the power injector 40' would be unable to execute an injection protocol).

Two attachment options for the tablet computer 700 are presented in FIG. 3A. Although both attachment options could be incorporated by single power injector 40', only one attachment option may be required in at least certain instances. One option is for the tablet computer 700 to be docked to the powerhead 50' of the power injector 40'. In this case the powerhead 50' would incorporate a docking connector or port 134 for each docking connector or port 740 used by the tablet computer 700. Such a powerhead 50' could then be characterized as a tablet computer docking station. Any appropriate latching mechanism or combination of latching mechanisms may be used to detachably retain the tablet computer 700 on the powerhead 50'. When the tablet computer 700 is docked to the powerhead 50', the tablet computer 700 blocks access to the graphical user interface 52 on the powerhead 50'. As such, it may be that there is only a single user input device for the power injector 40' at this time and in the form of the tablet computer 700.

Another attachment option is for the tablet computer 700 to be docked to the power injector 40' other than through the powerhead 50'. For instance, a docking station 130 may be supported by the stand 48 and may include a docking platform 132 having a docking connector or port 134 for each docking connector or port 740 used by the tablet computer 700. Any appropriate latching mechanism or combination of latching mechanisms may be used to detachably retain the tablet computer 700 on the docking platform 132.

The powerhead 50' of the power injector 40' of FIGS. 3A-B is mounted on the stand 48 in any appropriate manner (e.g., so as to be pivotable relative thereto). In the case of the first-noted attachment option, the tablet computer 700 would move collectively with the powerhead 50' as the powerhead 50' is moved relative to the stand 48 (e.g., where the powerhead 50' may be tilted upwardly for a fluid loading operation, an air purging operation, or both (with the discharge nozzle of each syringe installed on the powerhead 50' being positioned above horizontal)), and where the powerhead 50' may be tilted downwardly for execution of an injection (with the discharge nozzle of each syringe installed on the powerhead 50' being positioned below horizontal). In the case of the second noted attachment option, the tablet computer 700 would not move collectively with the powerhead 50' as the powerhead 50' is moved relative to the stand 48.

The stand 48 extends from a base 110. Any appropriate number of casters, rollers, wheels, tracks, or the like 114 may be utilized by the base 110 of the power injector 40' to provide portability for the power injector 40. The various casters 114 may be collectively characterized as a transport assembly 112 for the power injector 40. The powerhead 50', stand 48, and base 110 may be collectively referred to as an "injector module." This injector module may be characterized as in the form of an assembly of components that are not intended to be disconnected when transporting the power injector 40' from one location to another. The entirety of the injector module may be characterized as being movable by its incorporation of the transport assembly 112.

The base 110 may include an interior cavity 118 and as illustrated in FIG. 3B. A power pack 120 may be incorporated by the base 110 within this interior cavity 118. The power pack 120 may include an AC/DC converter 122, along with a communications module 124. Power may be transmitted from the AC/DC converter 122 to the communications module 124 over an appropriate link 126, if needed. Power may also be transmitted from the AC/DC converter 122 to the powerhead 50' in any appropriate manner. The power injector 40' could use or more on-board energy or power supplies of any appropriate type (e.g., one or more batteries).

Figure 4:
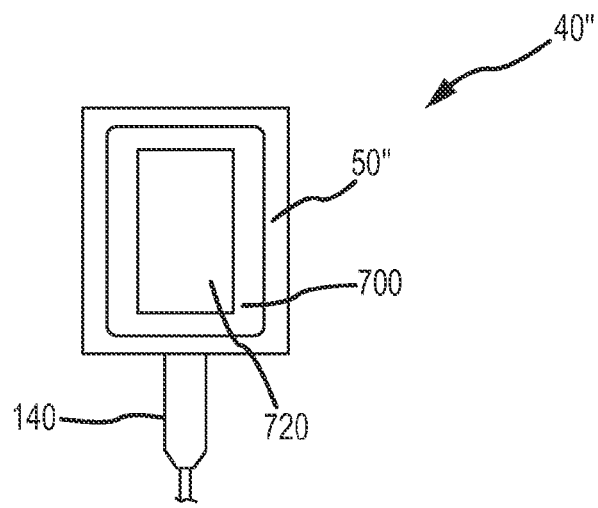
FIG. 4 is a plan view of a portion of a contrast media injector system, illustrating a tablet computer being connected to a powerhead of a single-head configuration.

Another embodiment of a contrast media injector system in the form of a power injector 40' is illustrated in FIG. 4. The primary difference between the power injector 40" of FIG. 4 and the power injector 40' of FIGS. 3A-B is that the power injector 40" utilizes a powerhead 50" of a single-head configuration (e.g., accommodating a single syringe 140). A tablet computer 700 is shown as being docked to the powerhead 50" in the manner discussed above in relation to the embodiment of FIGS. 3A-B. The powerhead 50" may include at least one user input device (other than the tablet computer 700) in some embodiments. The tablet computer 700 may be the only user input device in other embodiments (e.g., the powerhead 50" may be devoid of any user input device, other than the tablet computer 700).

Figure 5:
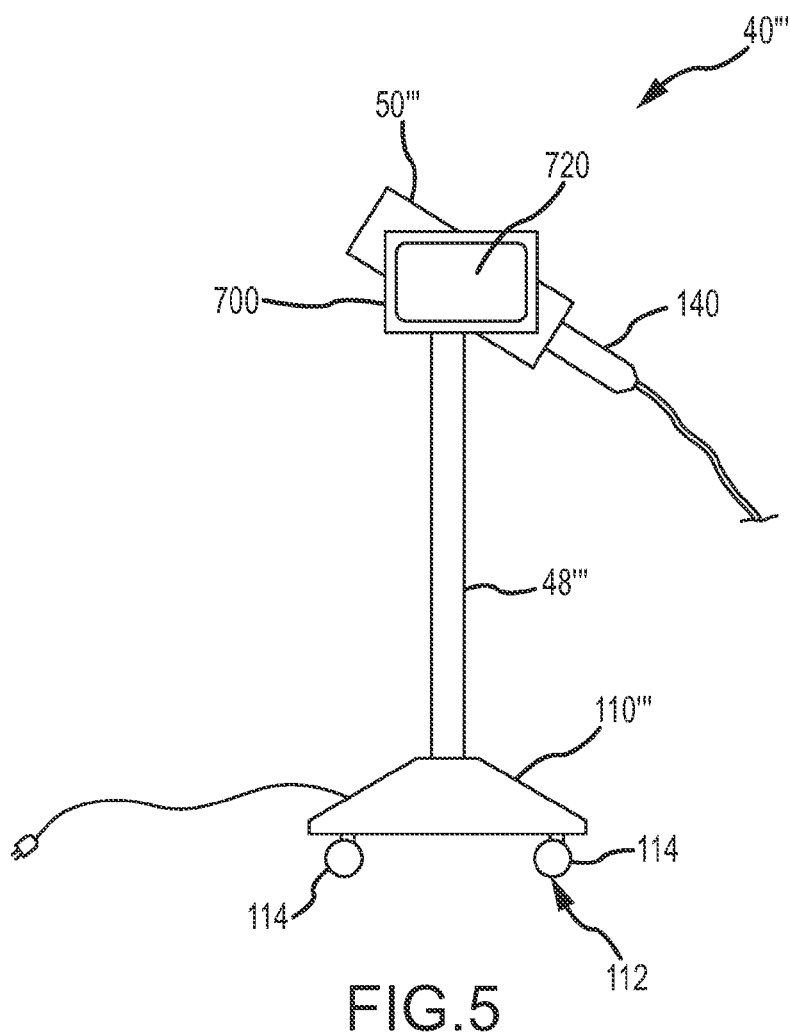
FIG. 5 is a side view of a contrast media injector system, illustrating a tablet computer being docked other than to a powerhead.

Another embodiment of a contrast media injector system in the form of a power injector 40''' is illustrated in FIG. 5. The power injector 40''' of FIG. 5 utilizes a powerhead 50''' of a single-head configuration (e.g., accommodating a single syringe 140), although it could be in the form of a dual-head configuration (e.g., FIGS. 3A-B). A tablet computer 700 is shown as being docked to the power injector 40''' other than at the powerhead 50''' in the case of the power injector 40'''. Tilting the powerhead 50''' relative to the stand 48''' does not change the position of the docked tablet computer 700 relative to the stand 48''' in the FIG. 5 configuration. The powerhead 50''' may include at least one user input device (other than the tablet computer 700) in some embodiments. The tablet computer 700 may be the only user input device in other embodiments (e.g., the powerhead 50''' may be devoid of any user input device, other than the tablet computer 700).

FIG. 6A illustrates one embodiment of a contrast media injector system 800 having an injector module 200 and at least one tablet computer 700. Although the injector system 800 could utilize multiple tablet computers 700, in one embodiment only one tablet computer 700 may be docked to the injector module 200 at a time. However, a multi-tablet computer configuration would allow one tablet computer 700 to be co-located with the injector module 200 (e.g., in an imaging room or suite) and would allow another tablet computer 700 to be at a different location (e.g., in a control room that is at least somewhat isolated from the injector module 200).

The injector module 200 includes a powerhead 300, an injector system control module 302 (which may be incorporated by the powerhead 300), a communication bus 400, a tablet docking station 500, a power pack 600, and a transport assembly 112 (e.g. FIGS. 3A and 3B). This collection of components for the injector module 200 is intended to be retained in a structurally assembled condition or state when transporting the injector module 200 from one location to another (e.g., the power pack 600 could be incorporated within the type of base 110 discussed above in relation to the embodiment of FIGS. 3A-B). The inclusion of the transport assembly 112 by the injector module 200 allows the entirety of the injector module 200 to be moved ms a single unit from one location to another. Other embodiments do not require a transport assembly 112 for the injector module 200 (e.g., the injector module 200 may be of a floor-mounted, wall-mounted, or ceiling-mounted type, for instance where the powerhead 300 is mounted (e.g., movably) on an appropriate support arm (e.g., movable in one or more dimensions)).

The powerhead 300 may be of any appropriate configuration (e.g., a single-head or multi-head configuration to accommodate a single or multiple syringes, respectively). The tablet docking station 500 may be incorporated in any appropriate manner, for instance in accordance with the embodiments of FIGS. 3A-B and FIG. 5. The power pack 600 may be incorporated by the injector module 200 in the manner of the power pack 120 discussed above in relation to the embodiment of FIGS. 3A-B, and may include one or more of an AC/DC converter 122, one or more on-board energy or power supplies of any appropriate type, and a communications module 124.

The tablet computer 700 communicates with the injector module 200 (more specifically, with the injector system control module 302) over an appropriate communications link 402 (e.g. wireless) and via the communication bus 400 for the injector module 200. Generally, a user may program injection parameters for the injector module 200 (e.g., define an injection protocol, for instance one or more phases and where each phase includes injection parameters such as a volume of contrast media to be injected and an injection flow rate, along with possibly one or more injection delays (e.g., a hold or a pause)), initiate the execution of a programmed injection protocol, terminate the execution of a programmed injection protocol, load fluid into one or more syringes utilized by the injector module 200, perform an air purging operation, undertake a manual injection, or the like, al through the tablet computer 700.

Two-way communications between the tablet computer 700 and the injector system control module 302 (via the communications link 402 and communication bus 400) are shown in relation to the illustrated embodiment by the double-headed arrows, although a one-way communication configuration could be utilized as well. The tablet computer 700 may be physically and detachably docked to the tablet docking station 500 (e.g., using one or more latching mechanisms to provide for detachable engagement of the tablet computer 700 with the injector module 200—such that the tablet computer 700 and the injector module 200 may be repeatedly connected and disconnected without damaging either component).

The contrast media injector system 800 may be configured to require that the tablet computer 700 be docked to the tablet computer docking station 500 in order to be able to control operation of and/or provide user input to the injector module 200 through communication with the injector system control module 302. The contrast media injector system 800 may be configured to allow the tablet computer 700 to not be docked to the tablet computer docking station 500, while using the tablet computer 700 to control operation of and/or provide user input to the injector module 200 through communication with the injector system control module 302. The contrast media injector system 800 may be configured to require an established communication ink between the tablet computer 700 and the injector system control module 302 in order for the injector module 200 to be operable for at least performing programmed injections (e.g., the injector module 200 may be operable in one or more other respects without an established communication link between the tablet computer 700 and the injector system control module 302). The contrast media injector system 800 may be configured to require an established communication link between the tablet computer 700 and the injector system control module 302 in order for the injector module 200 to be fully operable. The contrast media injector system 800 may be configured to require an established communication link between the tablet computer 700 and the injector system control module 302 in order for the injector module 200 to be operable in any respect.

FIG. 6A illustrates that the contrast media injector system 800 may be used by an imaging suite 980 having an imaging room 950 that is separated from a control room 960 by a barrier 970 of any appropriate type. This separation may not be required in all instances. In some embodiments, this barrier 970 may include radiation (e.g., alpha, beta and/or gamma) shielding, RF shielding, and/or any other type of material that may reduce the likelihood of undesired conditions that could hinder image acquisition.

The injector module 200 and the tablet computer 700 of the contrast media injector system 800 are shown in FIG. 6A as being located in the imaging room 950. An optional user-mountable user input device 760 for the injector system 800 is also presented in the FIG. 6A configuration. Generally, the user input device 760 may be worn by or attached to a user in any appropriate manner. When not operating the user input device 760, each of the user's hands are available to perform any number of tasks. As desired, user input may be provided to the user input device 760, which may then be transmitted to the tablet computer 700 over any appropriate communications link 402 (e.g., wirelessly, Bluetooth), and which may then be transmitted to the injector system control module 302 of the injector module 200. This may allow a user to control at least certain aspects of the operation of the injector module 200 without having to physically return to the tablet computer 700 to provide user input to the injector system control module 302.

A remote console 750, another tablet computer 700a, and another tablet docking station 500a are shown as being located in the control room 960 in the FIG. 6A configuration. Each of these components are optional in relation to the contrast media injector system 800 as discussed herein. Any such remote console 750 and second tablet computer 700a may be used to provide user input to the injector module 200 (more specifically, its injector system control module 302) over any appropriate communications link 402. The injector system 800 may be configured such that each of the tablet computer 700, the remote console 750, and the tablet computer 700a may be used to control operation of and/or provide user input to the injector module 200 through communication with the injector system control module 302 (e.g., in accordance with the functionality set forth above in relation to the tablet computer 700).

All permutations of the above-noted optional components of the contrast media injector system 800 may be utilized. The injector system 800 may use a single tablet computer 700 (i.e., no second tablet computer 700a), alone or in combination with a remote console 750. The injector system 800 may use a single tablet computer 700 (i.e., no second tablet computer 700a), alone or in combination with a remote console 750, and the tablet docking station 500 (both with and without the second tablet docking station 500a). The injector system 800 may use both the tablet computer 700 and the second tablet computer 700a, with or without a remote console 750, and the tablet docking station 500 (both with and without the second tablet docking station 500a).

The remote console 750 (e.g., a computer) of the contrast media injector system 800 may include a remote console display (not shown) and at least one user input device (not shown). Each user input device for the remote console 750 may be of any appropriate type, for instance, in the form of a keyboard, mouse, touch screen, joystick, trackball, or the like. Generally, a user may program injection parameters for the injector module 200 (e.g., define an injection protocol, for instance one or more phases and where each phase includes injection parameters such as a volume of contrast media to be injected and an injection flow rate, along with possibly one or more injection delays (e.g., a hold or a pause)) through one or more user input devices of the remote console 750.

FIG. 6B illustrates a variation of the contrast media injector system 800 of FIG. 6A. Corresponding components between the two embodiments are identified by common reference numerals. Those corresponding components that differ in at least some respect are identified by a "single prime" designation in the FIG. 6B embodiment. In the contrast media injector system 800' of FIG. 6B, the power pack 600' is no longer part of the injector module 200' (e.g., movement of the entirety of the injector module 200' through the transport assembly 112 is not intended to move the power pack 600'; the injector module 200' may be moved independently of the power pack 600". Although the power pack 600' may include at least one of an AC/DC converter 122 and a communications module 124, the power pack 600' is spaced from and is not structurally interconnected with the injector module 200' in this case (e.g., in accordance with the power pack 46 shown in FIG. 2A). Otherwise, the contrast media injector system 800' may otherwise be in accordance with the injector system 800 of FIG. 6A (e.g., it could utilize one or more tablet computers 700).

Figure 6C:
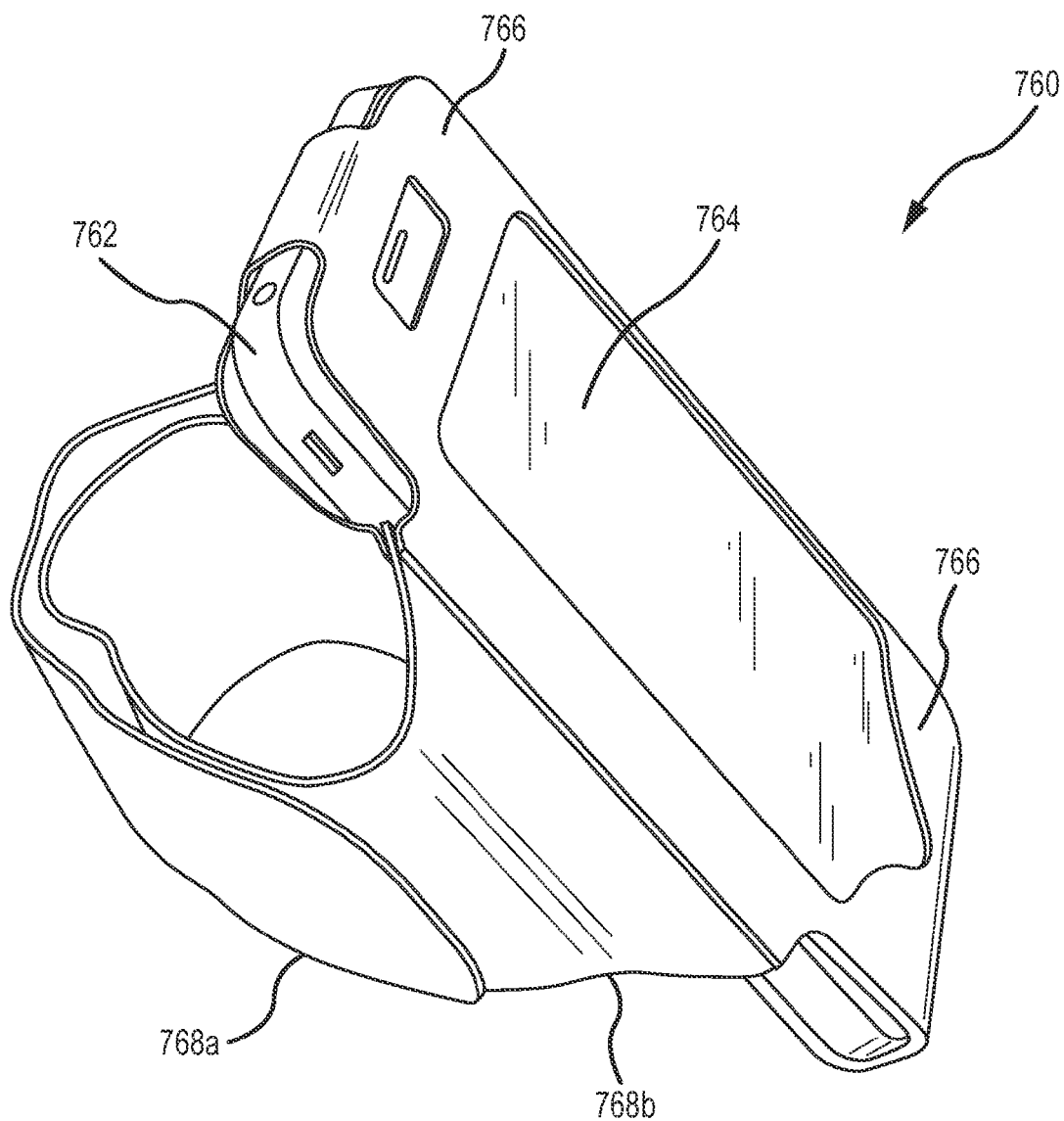
FIG. 6C is a perspective view of one embodiment of a user-mountable user input device that may be used to provide user input to a tablet computer used by a contrast media injector system.

Each of the contrast media injector system 800 (FIG. 6A) and the contrast media injector system 800' (FIG. 6B) may use at least one user-mountable user input device 760. Although this has been described in relation to providing input to a tablet computer 700 of an injector system, the user-mountable user input device 760 could be used to provide user input to any computer that in turn may be used to control operation of and/or provide user input to an injector module 200 through communication with its injector system control module 302. One embodiment of such a user input device is illustrated in FIG. 6C. Here the user input device 760 is in the form of a smart phone 762 (or personal digital assistant or PDA) that is disposed in a jacket or pocket 766 that may be secured to a user via a strap 768a and a strap 768b. These straps 768a, 768b may include Velcro®, snaps, a buckle, or any other way of securing the straps 768a, 768 relative to one another. The smart phone 762 includes a touchscreen 764. A user may operate the touchscreen 764 to communicate with a tablet computer 700 in accordance with the foregoing.

Figure 7A:
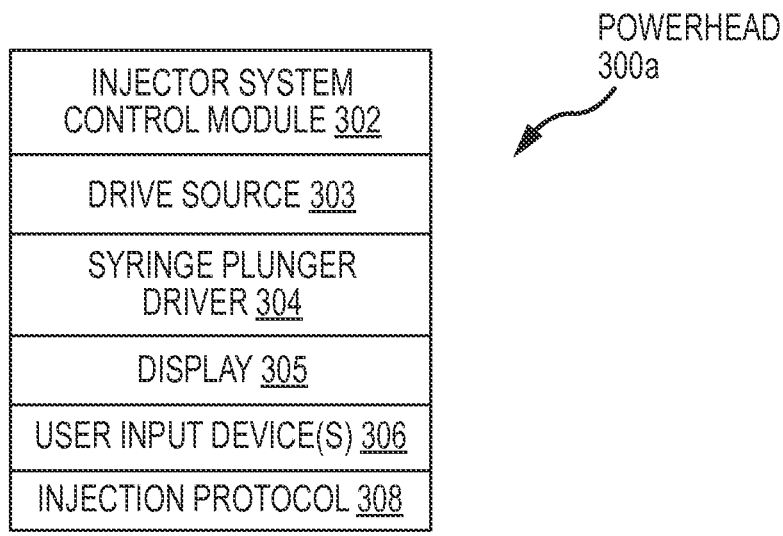
FIG. 7A is a block diagram of one embodiment of a powerhead that may be used by the contrast media injector systems of FIGS. 6A and 6B.
Figure 7B:
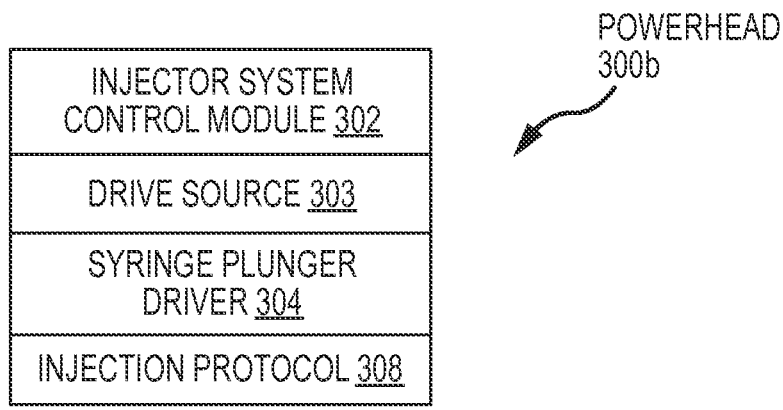
FIG. 7B is a block diagram of another embodiment of a powerhead that may be used by the contrast media injector systems of FIGS. 6A and 6B.

Two configurations for the powerhead 300 used by each of the injector systems 800, 800' of FIGS. 6A and 6B, respectively, are presented in FIGS. 7A and 7B. The powerhead 300a of FIG. 7A includes an injector system control module 302, at least one drive source 303 (e.g., a motor, for instance motor 58 discussed above in relation to the power injector 40), at least one syringe plunger driver 304 (e.g., syringe plunger driver 14 of power injector 10; syringe plunger driver 56 of power injector 40), a display 305, one or more user input devices 306, and a single injection protocol 308 that is stored on an appropriate computer-readable storage medium. The display 305 and user input device 306 may be in the form of a common touchscreen (e.g., a single structure could provide the functionality of both the display 305 and one or more user input devices 306). For a single-head configuration (e.g., where the powerhead 300a accommodates a single syringe), the powerhead 300a may include a single drive source 303 and a single syringe plunger driver 304. For a dual-head configuration (e.g., where the powerhead 300a accommodates two syringes), the powerhead 300a may include two drive sources 303 and two syringe plunger drivers 304. Other configurations may be appropriate.

The injection protocol 308 (stored on the powerhead 300a) may be programmed using a tablet computer 700 (e.g., using a touchscreen 720 of a tablet computer 700; using a touchscreen 764 of a user-mountable user input device 760 that communicates with a tablet computer 700), using a remote console 750 (including using a touchscreen 764 of a user-mountable user input device 760 that communicates with this remote console 750), using one or more user input devices 306 for the powerhead 300a, or any combination thereof. This programming may be done through communication with the injector system control module 302. User input from a tablet computer 700 (directly or from a user-mountable user input device 760 that communicates with a tablet computer 700) may be communicated to the injector system control module 302. The injector system control module 302 in turn may control operation of the drive source 303, which in turn controls movement of the syringe plunger driver 304 (e.g., by a programmed execution of the injection protocol 308).

As in the case of the powerhead 300a, the powerhead 300b of FIG. 7B includes an injector system control module 302, at least one drive source 303, at least one syringe plunger driver 304, and a single injection protocol 308 that is stored on an appropriate computer-readable storage medium. However, the powerhead 300b of FIG. 7B does not utilize either a display 305 or any user input device 306 of any kind (e.g., the powerhead 300b does not incorporate a touchscreen of any type). As such, the injector system 800/800' may be configured such that al data inputs used by the injector system control module 302 are required to be provided using only a tablet computer 700 that is part of the corresponding injector system 800/800' (directly or from a user-mountable user input device 760 that communicates with a tablet computer 700). For instance, it may be that the tablet computer 700 must be used to program the injection protocol 308 in such a configuration.

The injector system control module 302 may be characterized as a controller for all aspects of operation of the powerhead 300 of the corresponding injector system 800/800'. The injector system control module 302 may be configured such it is required to "see" a tablet computer 700 (e.g., a condition where the tablet computer 700 is in communication with the injector system control module 302; a condition where the tablet computer 700 responds to a prompt issued by/through the injector system control module 302) in order for the injector system control module 302 to allow for the execution of an injection protocol 308.

All signals that ultimately control operation of the powerhead 300 in a particular injector system 800/800' (as well as the injector system 800c discussed below in relation to FIG. 9 and the injector system 800" discussed below in relation to FIG. 11) may be transmitted from or through the injector system control module 302. For instance, the contrast media injector systems 800, 800', 800", 800c may utilize a master/slave control architecture, where the powerhead 300 (more specifically the injector system control module 302) of a particular injector system 800/800'/800"/800c is the "master" and where each tablet computer 700 and each user-mountable user input device 760 of this same injector system 800/800'/800"/800c is a "slave." The powerhead 300 (more specifically the injector system control module 302) of a particular injector system 800/800'/800"/800c may be characterized as a master node in a control architecture, while each tablet computer 700 and user-mountable user input device 760 of this same injector system 800/800'/800"/800c may be characterized as a requestor node. Although inputs may be provided to a particular injector system 800/800'/800"/800c through one of its tablet computers 700 and/or through a user-mountable user input device 760, these inputs are provided to the injector system control module 302 of this same injector system 800/800'/800"/800c to control operation of its powerhead 300.

Figure 8:
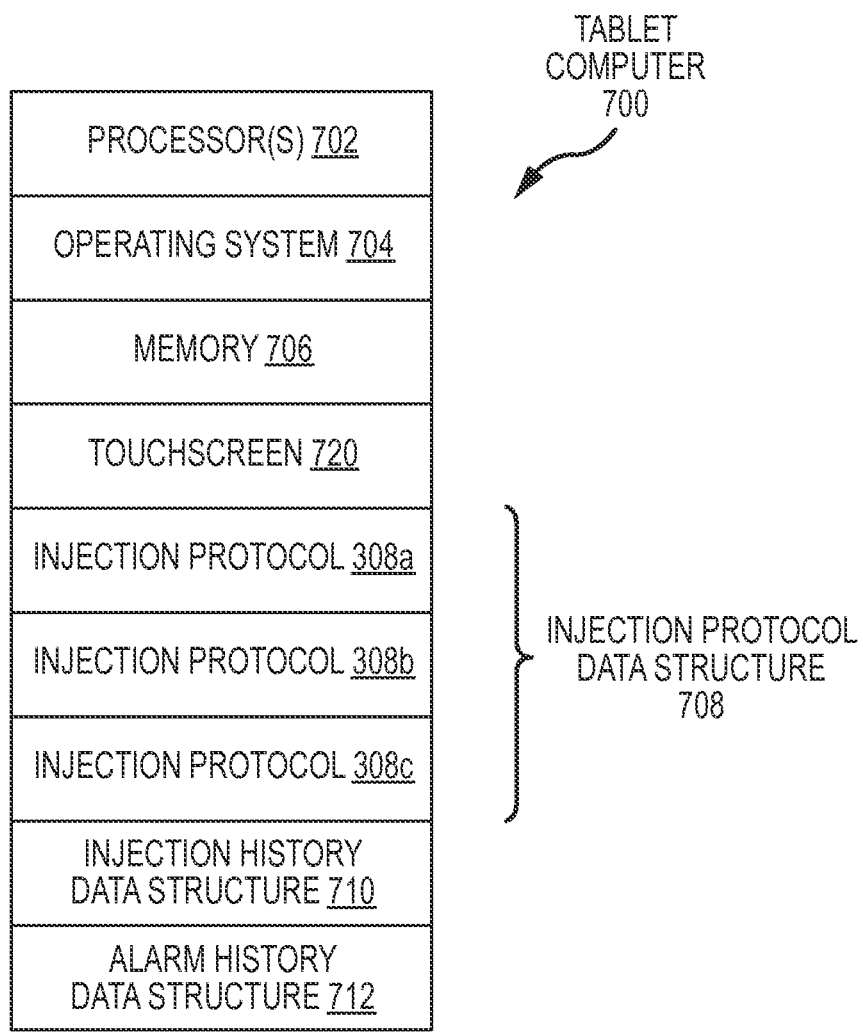
FIG. 8 is a block diagram of one embodiment of a tablet computer that may be incorporated by a contrast media injector system.

A functional schematic of the above-noted tablet computer 700 is presented in FIG. 8. The tablet computer 700 includes one or more processors 702, an operating system 704, memory 706 of any appropriate type or types (e.g., a computer-readable storage medium), the above-noted touchscreen 720, an injection protocol data structure 708, an injection history data structure 710, and an alarm history data structure 712. Each of these data structures 708, 710, and 712 may be configured/stored in the memory 706.

The injection protocol data structure 708 includes a plurality stored injection protocols 308—three being shown in relation to the illustrated embodiment and in the form of injection protocols 308a-c. Any appropriate number of multiple injection protocols 308 may be stored in the injection protocol data structure 708. Generally, an injection protocol 308 may be used to provide for programmed operation of the corresponding injector system 800/800' (e.g., programmed operation of its powerhead 300). An injection protocol 308 may have one or more phases, with each phase including injection parameters such as an amount of fluid to be injected and an injection flow rate, as well as possibly one or more injection delays (sometimes referred to as "holds" and/or "pauses"), and each of which can be of finite or infinite duration.

Multiple injection protocols 308 may be stored by the tablet computer 700 of a particular injector system 800/800', namely in the injection protocol data structure 708 for this tablet computer 700. Only a single injection protocol 308 may be stored on the powerhead 300 of a particular injector system 800/800'. The powerhead 300 of a particular injector system 800/800' does not incorporate the injection protocol data structure 708. However, the to powerhead 300 (through the injector system control module 302) of a particular injector system 800/800' may retrieve an injection protocol 308 stored in the injection protocol data structure 708 of the tablet computer 700 from this same injector system 800/800', and may then retain this single injection protocol 308 in its memory to control operation of the powerhead 300 for this same injector system 800/800'.

The injection history data structure 710 for a tablet computer 700 of a particular injector system 800/800' includes data from multiple executions of one or more of the injection protocols 308 from the corresponding injection protocol data structure 708. These "multiple executions" could be of the same injection protocol 308 from the corresponding injection protocol data structure 708. These "multiple executions" could be at least one execution of two or more of the injection protocols from the corresponding injection protocol data structure 708. In one embodiment, data on the most recent "x" injection protocols 308 from the injection protocol data structure 708 that were executed by the corresponding injector system 800/800' are stored in the injection history data structure 710 of an associated tablet computer 700 (where "x" is an appropriate integer). The injection history data structure 710 is not incorporated by the powerhead 300 of the corresponding injector system 800/800'.

The alarm history data structure 712 for a tablet computer 700 of a particular injector system 800/800' includes data relating to alarm conditions that were encountered during the execution of one or more of the injection protocols 308 from the corresponding injection protocol data structure 708. In one embodiment data on the most recent "x" alarm conditions are stored in the alarm history data structure 712 of an associated tablet computer 700 (where "x" is an appropriate integer). The alarm history data structure 712 is not incorporated by the powerhead 300 of the corresponding injector system 800/800'.

Figure 9:
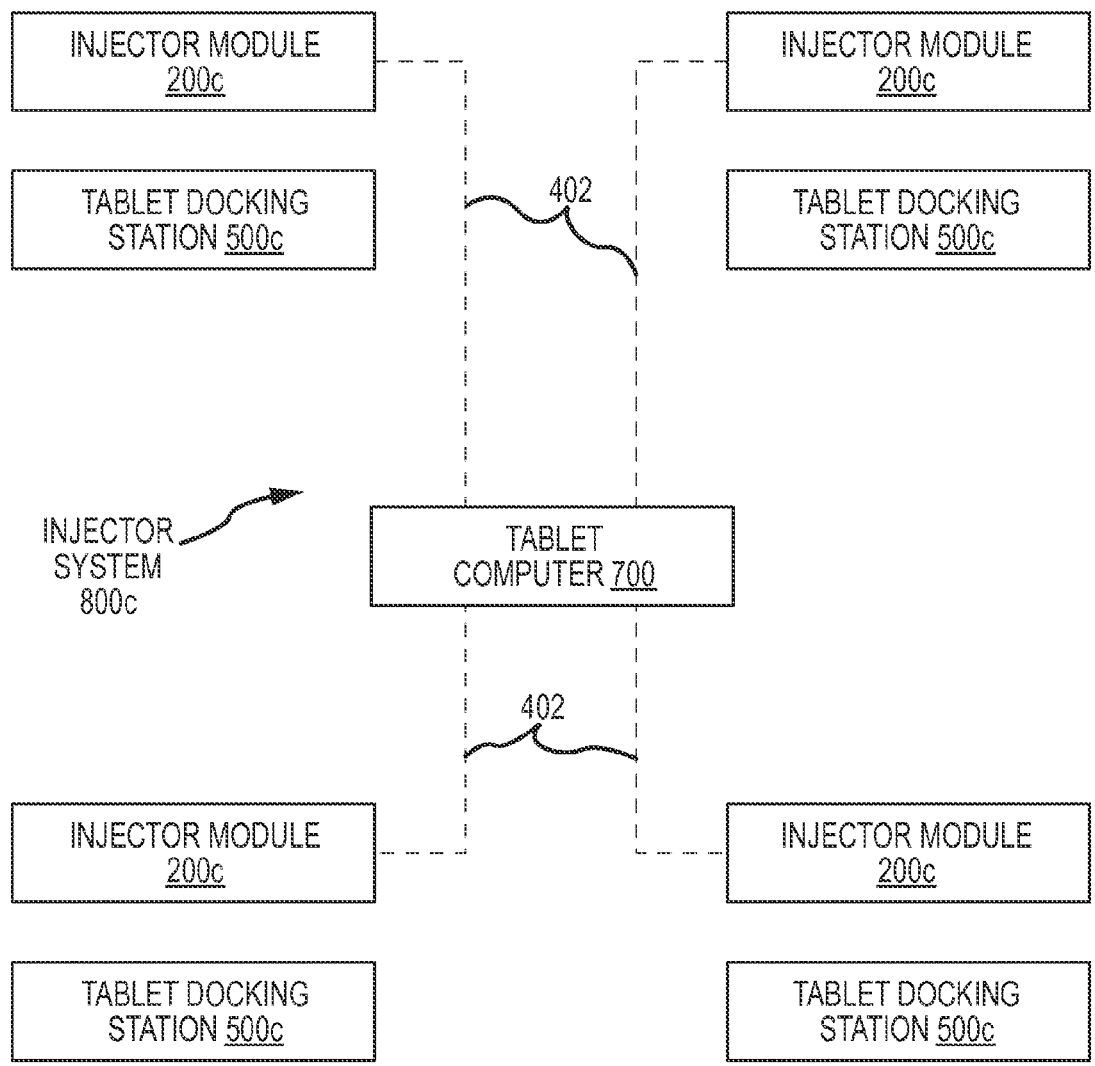
FIG. 9 is a block diagram of one embodiment of a contrast media injector system where a tablet computer is in communication with multiple injector modules.

FIG. 9 illustrates another embodiment of a contrast media injector system 800c where a given tablet computer 700 communicates with and/or controls operation of multiple injector modules 200c (four in the illustrated embodiment) over an appropriate communications link 402. A given tablet computer 700 may communicate with and/or control operation of any appropriate number of different injector modules 200c. Each injector module 200c could be located in a different imaging room, although such is not required. Each injector module 200c may be associated with one or more tablet docking stations 500c, including where a given injector module 200c incorporates a tablet docking station 500c (e.g., in accordance with the powerhead 300 shown in FIGS. 6A and 6B), as well as where the injector module 200c and the tablet docking station 500c are separate components (e.g., in accordance with tablet computer 700a and tablet docking station 500a in the embodiments of FIGS. 6A and 6B).

A contrast media injector system 800a having a communications module 660 of the type that may be utilized by the power packs 120, 600, and 600' discussed above is presented in FIG. 10A. Generally, the injector system 800a could be of the configuration shown in the embodiment of FIG. 6A, or could be of the configuration shown in the embodiment of FIG. 6B—where a tablet computer 700 may be docked to a tablet docking station 500 of the associated injector module 200/200'. Generally, the communications module 660 allows the injector system 800a to communicate with one or more external devices (e.g., an imaging system 900, a hospital information system (HIS) 910, a contrast media storage/dispensing unit 920, a radiological information system (RIS) 930, a picture archive and communication system (PACS) 940, or the like (e.g., a pharmacy information system (PhIS), a hospital management system (HMS)). The injector communications module 660 may be configured to convert data from at least one format into at least one other format, namely to allow communication between the injector system 800a and various other components that are not part of the injector system 800a.

The communications module 660 may be configured to communicate with an imaging system 900 over a communication link 678 of any appropriate type (e.g., a wired connection; an appropriate data cable; wirelessly). Communications between the contrast media injector system 800a and the imaging system 900 are directed through the injector communications module 660. The contrast media injector system 800a may utilize one CAN-compliant format (e.g., CAN 2.0A), while the imaging system 900 may utilize another CAN-compliant format (e.g., CiA 425). Contrast administration data from the contrast media injector system 800a may be converted from one format to another format by the injector communications module 660 for transmission to the Imaging system 900. In one embodiment, two-way communications between the contrast media injector system 800a and the imaging system 900 are allowed through the injector communications module 660 (e.g., such that the injector communications module 660 can provide both a CAN 2.0A to CiA 425 conversion, as well as a CiA 425 to CAN 2.0A conversion). However, the communications module 660 could be configured such that there may only be one-way communications between the contrast media injector system 800a and the imaging system 900 (in either direction).

The contrast media injector system 800a may communicate with the HIS 910 over a communication link 674 of any appropriate type (e.g., a wired connection; an appropriate data cable; wirelessly). Communications between the contrast media injector system 800a and the HIS 910 are directed through the injector communications module 660. The contrast media injector system 800a may utilize one CAN-compliant format (e.g., CAN 2.0A), while the HIS 910 may utilize an HL-7-compliant format. Contrast administration data from the contrast media injector system 800a may be converted from one format to another format by the injector communications module 660 for transmission to the HIS 910 (e.g., CAN 2.0A to HL-7).

The contrast media injector system 800a may communicate with the contrast media storage/dispensing unit 920 (e.g., CMSDU 920; a contrast media "vending machine") over a communication link 676 of any appropriate type (e.g., a wired connection; an appropriate data cable; wirelessly). Communications between the contrast media injector system 800a and the contrast media storage/dispensing unit 920 are directed through the injector communications module 660. The contrast media injector system 800a may utilize one CAN-compliant format (e.g., CAN 2.0A), while the contrast media storage/dispensing unit 920 may utilize an HL-7-compliant format. Contrast administration data from the contrast media injector system 800a may be converted from one format to another format by the injector communications module 660 for transmission to the contrast media storage/dispensing unit 920 (e.g., CAN 2.0A to HL-7).

The contrast media injector system 800a may communicate with the PACS 940 over a communication ink 680 of any appropriate type (e.g., a wired connection; an appropriate data cable; wirelessly). Communications between the contrast media injector system 800a and the PACS 940 are directed through the injector communications module 660. The contrast media injector system 800a may utilize one CAN-compliant format (e.g., CAN 2.0A), while PACS 940 may utilize a DICOM ("Digital imaging and Communications in Medicine") format. Contrast administration data from the contrast media injector system 800a may be converted from one format to another format by the injector communications module 660 for transmission to the PACS 940 (e.g., CAN 2.0A to DICOM).

The contrast media injector system 800a may communicate with the RIS 930 over a communication link 682 of any appropriate type (e.g., a wired connection; an appropriate data cable; wirelessly). Communications between the contrast media injector system 800a and the RIS 930 are directed through the injector communications module 660. The contrast media injector system 800a may utilize one CAN-compliant format (e.g., CAN 2.0A), while the RIS 930 may utilize an HL-7-compliant format. Contrast administration data from the contrast media injector system 800a may be converted from one format to another format by the injector communications module 660 for transmission to the RIS 930 (e.g., CAN 2.0A to HL-7).

The above-noted data conversions by the communications module 660 may be implemented through what may be characterized as a data converter unit 662. The contrast media injector system 800a utilizes an injector communication bus 400 for transmitting data throughout the contrast media injector system 800a. The injector communication bus 400 may utilize a first CAN-compliant format for data communications, such as a CAN 2.0A. In any case, the injector system control module 302 of the contrast media injector system 800a may communicate with the data converter unit 662 over a communication ink 672, which may be part of the communications bus 400. In the illustrated embodiment, the data converter unit 662 includes three different data conversion modules. Any appropriate number of data conversion modules may be utilized by the data converter unit 662.

The data converter unit 662 includes a first data conversion module 614 that is operatively interconnected with the injector communication bus 400 of the contrast media injector system 800a (e.g., via the communication ink 672, and which may actually be part of the injector communication bus 606). Generally, the first data conversion module 614 converts contrast administration data from a first CAN-compliant format (e.g., CAN 2.0A) into an HL-7-compliant format. This may be undertaken in any appropriate manner.

The first data conversion module 614 may utilize one or more processors 620 of any appropriate type. One or more processors 620 may be used for the data conversion provided by the first data conversion module 614. One or more processors 620 may be used by the first data conversion module 614 to process requests for contrast administration data received by the first data conversion module 614 from the HIS 910. Multiple processors 620 may be arranged in any appropriate processing architecture for purposes of the first data conversion module 614.

The first data conversion module 614 may utilize one or more data storage devices 622 of any appropriate type (e.g., hard drive, solid state memory, flash memory, non-volatile ram). Multiple data storage devices 622 may be arranged in any appropriate data storage architecture. Generally, contrast administration data may be transmitted to the first data conversion module 614 and stored on one or more of its data storage devices 622. The contrast administration data that is provided to the first data conversion module 614 may be of any appropriate type (e.g., predefined) and may be provided to the first data conversion module 614 on any appropriate basis (e.g., on a real-time basis; intermittently on a batch-type basis, for instance at the end of a programmed injection).

The first data conversion module 614 may be characterized as including a first communication port 624, a CMSDU communication port 628, and a RIS communication port 629. The first communication port 624 of the first data conversion module 614 is operatively interconnected with the HIS 910 through the communication ink 674. The CMSDU communication port 628 of the first data conversion module 614 is operatively interconnected with the contrast media storage/dispensing unit 920 through the communication link 676. The RIS communication port 629 of the first data conversion module 614 is operatively interconnected with the RIS 930 through the communication link 682.

The first data conversion module 614 may be characterized as including a first communication node 616 associated with the injector communication bus 400, a second communication node 618 associated with the first communication port 624, a communication node 618' associated with the CMSDU communication port 628, and a communication node 618' associated with the RIS communication port 629. In one embodiment, the HIS 910 is able to send communications (e.g., a request for contrast administration data) to the first data conversion module 614 through the second communication node 618 and the first communication port 624. However, the first data conversion module 614 may be configured so as to not allow communications from the HIS 700 to proceed past the first communication node 616 to the injector communication bus 606 of the contrast media injector system 602. The first communication port 624 may therefore be characterized as being of a pull-type configuration (e.g., contrast 30 administration data may be 'pulled' from the first data conversion module 614 by the HIS 910). Stated another way, the first data conversion module 614 may be configured to transmit contrast administration data to the HIS 910 only in response to a request for contrast administration data submitted by the HIS 910 to the first data conversion module 614—the contrast media injector system 602 does not automatically "push" contrast administration data to the HIS 910. One or more processors 620 of the first data conversion module 614 may receive such a request for contrast administration data from the HIS 910, may retrieve the relevant contrast administration data from one or more data storage devices 622 of the first data conversion module 614, and may transmit (or allow the transmission of) the retrieved contrast administration data to the HIS 910 through the first communication port 624 of the first data conversion module 614 and communication ink 674. In other embodiments, the first data conversion module 614 may allow for two-way communication between the contrast media injector system 602 and the HIS 910 (e.g., using a push configuration; using a push/pull configuration).

The data converter unit 662 includes a second data conversion module 630 that is operatively interconnected with the injector communication bus 400 of the contrast media injector system 800a (e.g., via the communication link 672, which may actually be part of the injector communication bus 400). Generally, the second data conversion module 630 converts contrast administration data between a first CAN-compliant format (e.g., CAN 2.0A; associated with the injector communication bus 400 of the contrast media injector system 800a) and a second CAN-compliant format (e.g., CiA 425; associated with the imaging system 900). This may be undertaken in any appropriate manner. The second data conversion module 630 may be configured to provide for a conversion of commands that may be sent between the powerhead 300 and the imaging system 900.

The second data conversion module 630 may utilize one or more processors 620 of any appropriate type. One or more processors 620 may be used for the data conversion provided by the second data conversion module 630. One or more processors 620 may be used to process requests for contrast administration data received by the second data conversion module 630 from the imaging system 900. Multiple processors 620 may be arranged in any appropriate processing architecture for purposes of the second data conversion module 630.

The second data conversion module 630 may utilize one or more data storage devices 622 of any appropriate type. Multiple data storage devices 622 may be arranged in any appropriate data storage architecture. Generally, data may be transmitted to the second data conversion module 630 and stored on one or more of its data storage devices 622 for use in conjunction with communications between the contrast media injector system 800a and the imaging system 900.

The second data conversion module 630 may be characterized as including a second communication port 638. The second communication port 638 of the second data conversion module 630 is operatively interconnected with the imaging system 900 through the communication link 678. The second data conversion module 630 may be characterized as including a first communication node 632 associated with the injector communication bus 400, and a second communication node 634 associated with the second communication port 638. In one embodiment, the second data conversion module 630 is configured to allow two-way communications between the contrast media injector system 800a and the imaging system 900. For example, communications may be sent by the imaging system 900 to the contrast media injector system 800a (e.g., the powerhead 300 thereof) through the second data conversion module 630 (where the communication is converted from one CAN-compliant format (e.g., CiA 425) to another CAN-compliant format (e.g., CAN 2.0A)) and communication link 672. Similarly, communications may be sent from the contrast media injector system 800a (e.g., the powerhead 300 thereof) to the imaging system 900 through the communication link 672, second data conversion module 630 (where the communication is converted from one CAN-compliant format (e.g., CAN 2.0A) to another CAN-compliant format (e.g., CiA 425)), and communication link 678.

The data converter unit 662 may include a third data conversion module 640 that is operatively interconnected with the injector communication bus 400 of the contrast media injector system 800a (e.g., via the communication link 672, which may actually be part of the injector communication bus 400). Generally, the third data conversion module 640 converts contrast administration data from a first CAN-compliant format (e.g., CAN 2.0A; associated with the injector communication bus 606 of the contrast media injector system 800*a*) to a PACS-compliant format (e.g., DICOM; associated with the PACS 710). This may be undertaken in any appropriate manner.

The third data conversion module 640 may utilize one or more processors 620 of any appropriate type. One or more processors 620 may be used for the data conversion provided by the third data conversion module 640. One or more processors 620 may be used to process requests for contrast administration data received by the third data conversion module 640 from the PACS 940. Multiple processors 620 may be arranged in any appropriate processing architecture for purposes of the third data conversion module 640.

The third data conversion module 640 may utilize one or more data storage devices 622 of any appropriate type. Multiple data storage devices 622 may be arranged in any appropriate data storage architecture. Generally, data may be transmitted to the third data conversion module 640 and stored on one or more of its data storage devices 622 for use in conjunction with communications between the contrast media injector system 800*a* and the PACS 940.

The third data conversion module 640 may be characterized as including a PACS communication port 646. The PACS communication port 646 of the third data conversion module 640 is operatively interconnected with the PACS 940 through the communication ink 680. The third data conversion module 640 may be characterized as including a first communication node 642 associated with the injector communication bus 400, and a second communication node 644 associated with the PACS communication port 646. In one embodiment, the third data conversion module 640 is configured to allow two-way communications between the contrast media injector system 800*a* and the PACS 940. For example, communications may be sent by the PACS 940 to the contrast media injector system 800*a* (e.g., the powerhead 300 thereof) through the third data conversion module 640 (where the communication is converted from a PACS-compliant format (e.g., DICOM) to a CAN-compliant format (e.g., CAN 2.0A)) and communication link 680. Similarly, communications may be sent from the contrast media injector system 800*a* (e.g., the powerhead 300 thereof) to the PACS 940 through the communication link 672, third data conversion 30 module 640 (where the communication is converted from a CAN-compliant format (e.g., CAN 2.0A) to a PACS-compliant format (e.g., DICOM)), and communication ink 680.

Figure 10A:
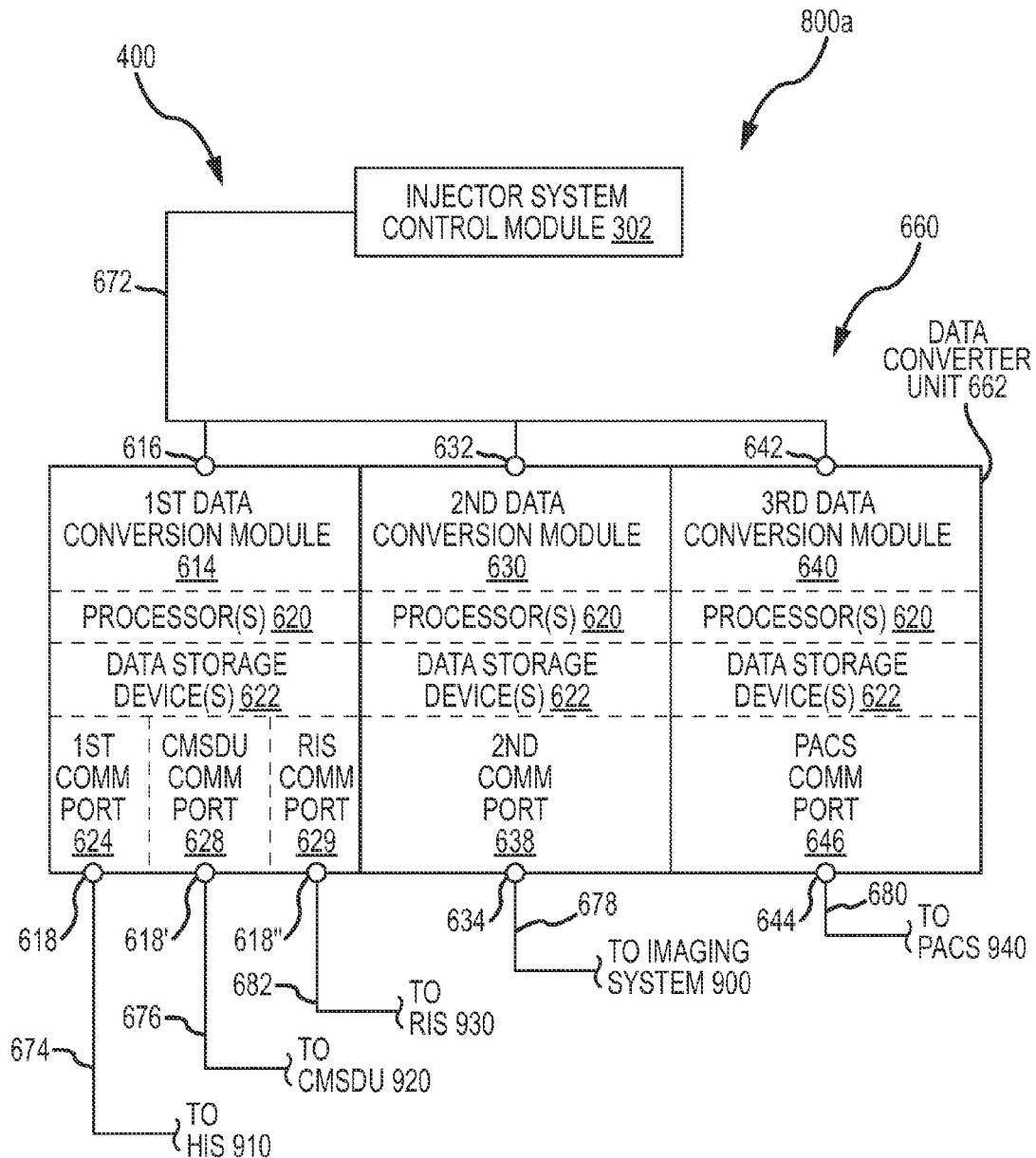
FIG. 10A is a functional schematic of one embodiment of a communications module for a contrast media injector system.

The first data conversion module 614, second data conversion module 630, and third data conversion module 640 may be characterized as being interconnected in parallel (as opposed to being in series) in the FIG. 10A configuration. Communications from the injector communication bus 400 may be simultaneously directed to each of the first data conversion module 614, second data conversion module 630, and third data conversion module 640. The first data conversion module 614, second data conversion module 630, and third data conversion module 640 may be characterized as being part of a common structure (e.g., the data converter unit 662) or as being disposed within a common housing (a housing for the data converter unit 662).

A contrast media injector system 800*b* having a communications module 660' of the type that may be utilized by the power packs 120, 600, and 600' discussed above is presented in FIG. 10B. The injector system 800*b* could be of the configuration shown in the embodiment of FIG. 6A, or could be of the configuration shown in the embodiment of FIG. 6B—where a tablet computer 700 may be docked to a tablet docking station 500 of the associated injector module 200/200'. Generally, the communications module 660' allows the injector system 800*b* to communicate with one or more external devices (e.g., an imaging system 900, a hospital information system (HIS) 910, a contrast media storage/dispensing unit 920, a radiological information system (RIS) 930, a picture archive and communication system (PACS) 940, or the like (e.g., a pharmacy information system (PIS), a hospital management system (HMS)). The injector communications module 660' may be configured to convert data from at least one format into at least one other format, namely to allow communication between the injector system 800*b* and various other components that are not part of the injector system 800*b*.

Figure 10B:
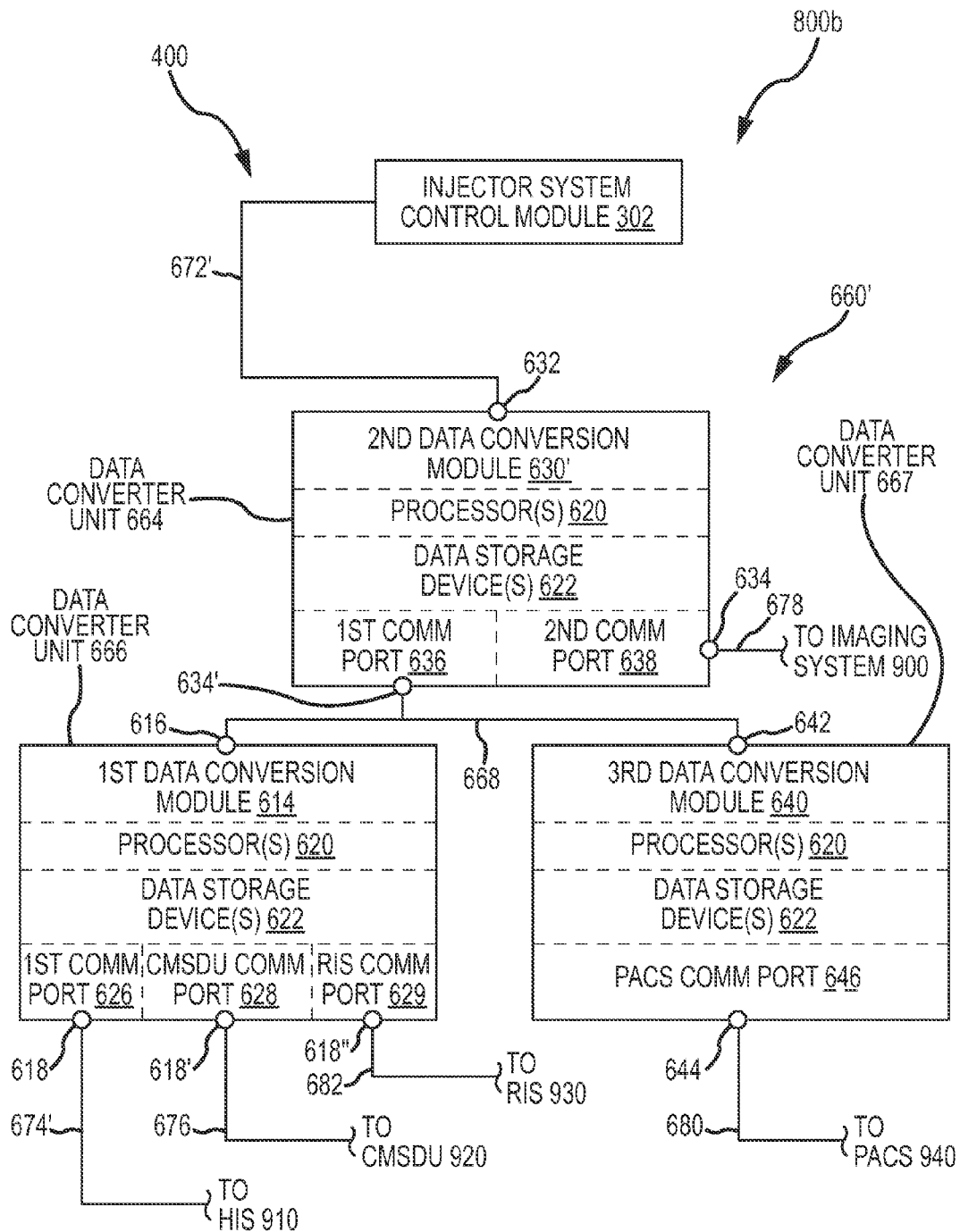
FIG. 10B is a functional schematic of another embodiment of a communications module for a contrast media injector system.

The injector communications module 660' of FIG. 10B is a variation of the injector communications module 660 discussed above in relation to FIG. 10A. Corresponding components between the embodiments of FIGS. 10A and 10B are identified by the same reference numeral. Those corresponding components that differ in at least some respect are identified by a "single prime" designation in FIG. 10B.

The injector communications module 660' of FIG. 10B utilizes each of the above-discussed first data conversion module 614 and third data conversion module 640, along with a modified second data conversion module 630'. Moreover, the injector communications module 660' of FIG. 10B utilizes a different arrangement of these components. Generally, the second data conversion module 630' is connected in series with the first data conversion module 614, and is also connected in series with the third data conversion module 640 (e.g., where the first data conversion module 614 is incorporated by a data converter unit 666, and where the third data conversion module 640 is incorporated by a date converter unit 667). As in the case of the FIG. 10A embodiment, the first data conversion module 614 and third data conversion module 640 may be connected in parallel.

The second data conversion module 630' converts contrast administration data between a first CAN-compliant format (e.g., CAN 2.0A; associated with the injector communication bus 400 of the contrast media injector system 800*b*) and a second CAN-compliant format (e.g., CiA 425; associated with the imaging system 900). This data conversion may be undertaken in any appropriate manner. However, in the FIG. 10B configuration, the injector communication bus 400 only communicates directly with the second data conversion module 630' (and therefore the communication link 672' between the injector communications module 660' and the powerhead 300 uses the noted "single prime" designation—the communication link 672' does not extend directly to either the first data conversion module 614 or the third data conversion module 640).

The contrast media injector system 800*b* and imaging system 900 continue to communicate through the second data conversion module 630' in the manner discussed above for the FIG. 10A embodiment. However, in order to allow the injector communication bus 400 to also communicate with each of the first data conversion module 614 and the third data conversion module 640, the second data conversion module 630' includes a first communication port 636 and a communication link 668. A second communication node 634' may be characterized as being associated with the first communication port 636 of the second data conversion module 630'.

The configuration and functionality of each of the first data conversion module 614 and the third data conversion module 640 in the FIG. 10B embodiment remains in accordance with the FIG. 10A embodiment. However, contrast administration data may be transmitted from the injector communication bus 400 through the first communication port 636 of the second data conversion module 630' (where a conversion from one CAN-compliant format to another CAN-compliant format occurs), and then may be transmitted over the communication ink 668 to one or both of the first data conversion module 614 and the third data conversion module 640 in the FIG. 10B configuration (where further conversions are undertaken in accordance with the foregoing).

Figure 11:
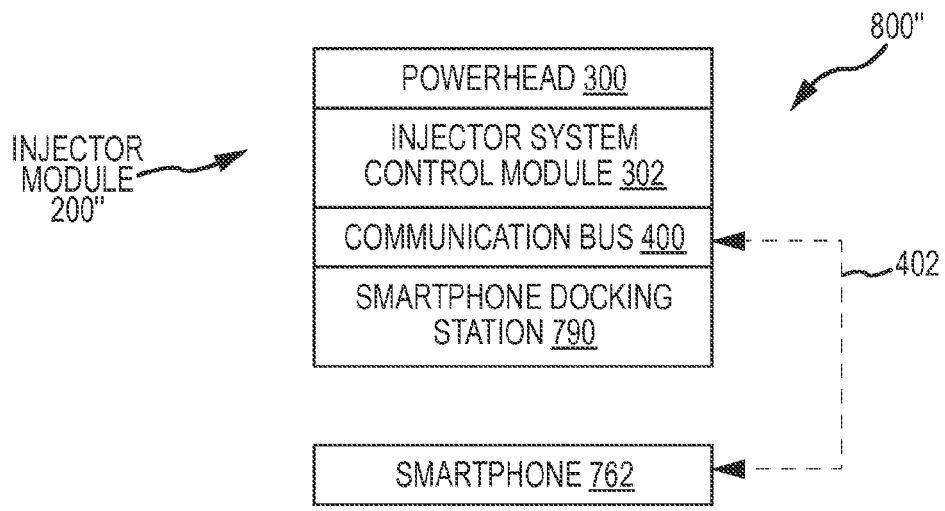
FIG. 11 is a block diagram of one embodiment a contrast media injector system that uses a smart phone.

FIG. 11 illustrates one embodiment of a contrast media injector system 800" having an injector module 200" and at least one smart phone 762. The injector module 200" may be of any appropriate configuration, including without limitation where the injector module 200" is configured so as to not utilize any tablet docking station 500 (e.g., for instance, for the case where the injector system 800" does not utilize any tablet computers 700). However, the injector module 200" could be in the form of the injector module 200 of FIG. 6A or in the form of the injector module 200' of FIG. 6B (whether or not the injector system 800" actually utilizes one or more tablet computers 700 in each such instance). As such, the injector module 200" may be configured to include a tablet docking station 500 (whether or not the injector system 800" actually utilizes one or more tablet computers 700).

The contrast media injector system 800" may utilize at least one tablet computer 700, may utilize a remote console 750, may include at least one user input device on the injector module 200", or any combination thereof. Each tablet computer 700, smart phone 762, and remote console 750 that may be utilized by the contrast media injector system 800" may communicate directly with the injector module 200" (e.g., the smart phone 762 need not "pass through" a tablet computer 700 to communicate with the injector module 200" in the case of the injector system 800"). The injector module 200" and the smart phone 762 may be co-located in an imaging room (e.g., such as the imaging room 950 discussed above), while at least one of a remote console 750 and a tablet computer(s) 700 may be located in a control room (e.g., such as the control room 960 discussed above), which again may be separated from the imaging room by an appropriate barrier (e.g., such as the barrier 970 discussed above). One embodiment has each smart phone 762 being the only user input (s) for the injector system 800", other than any user input device incorporated by the injector module 200" (e.g., the injector system 800" may be configured so as to not utilize any tablet computer(s) 700 and so as to not utilize a remote console 750). Only one or more smart phones 762 are available as a user input device(s) for the injector system 800" in another embodiment (e.g., the injector system 800" may be configured so as to not utilize any tablet computer(s) 700, so as to not utilize a remote console 750, and so as to not utilize any user input device for the injector module 200).

The injector module 200" of the contrast media injector system 800" of FIG. 11 includes at least a powerhead 300, an injector system control module 302 (which may be incorporated by the powerhead 300), a communication bus 400, and an optional docking station 790 for a smart phone 762. The injector module 200" may or may not include a transport assembly 112. The powerhead 300 may be of any appropriate configuration (e.g., a single-head or multi-head configuration to accommodate a single or multiple syringes, respectively). The powerhead 300 could be in the form of the powerhead 300a presented in FIG. 7A, or could be in the form of the powerhead 300b presented in FIG. 7B.

The smart phone 762 communicates directly with the injector module 200" (more specifically, with the injector system control module 302) over an appropriate communications link 402 (e.g., wireless; a cellular communication system) and via the communication bus 400 for the injector module 200" in the case of the injector system 800" of FIG. 11. Generally, a user may program injection parameters for the injector module 200" (e.g., define an injection protocol, for instance one or more phases and where each phase includes injection parameters such as a volume of contrast media to be injected and an injection flow rate, along with possibly one or more injection delays (e.g., a hold or a pause)), initiate the execution of a programmed injection protocol, terminate the execution of a programmed injection protocol, load fluid into one or more syringes utilized by the injector module 200", perform an air purging operation, undertake a manual injection, or the like, all through the smart phone 762.

Two-way communications between the smart phone 762 and the injector system control module 302 (via the communications link 402 and communication bus 400) are shown in relation to the illustrated embodiment by the double-headed arrows, although a one-way communication configuration could be utilized as well. The smart phone 762 may be physically and detachably docked to the smart phone docking station 790 of the injector module 200" (e.g., using one or more latching mechanisms to provide for detachable engagement of the smart phone 762 with the injector module 200"; such that the smart phone 762 and the injector module 200" may be repeatedly connected and disconnected without damaging either component). The smart phone 762 may be used by the injector system 800" in the form of the above-described user-mountable user input device 760 or may be used independently of the above-discussed carrier in the form of a jacket/pocket 766 and strap 768.

The contrast media inceptor system 800" may be configured so as to allow the smart phone 762 to not be docked to the smart phone docking station 790 and yet still allow the smart phone 762 to control operation of and/or provide user input to the injector module 200" through communication with the injector system control module 302 in accordance with the foregoing. The contrast media injector system 800" may be configured so as to require the smart phone 762 to be docked to the smart phone docking station 790 in order for the smart phone 762 to control operation of and/or provide user input to the injector module 200" through communication with the injector system control module 302 in accordance with the foregoing. The contrast media injector system 800" may be configured to require an established communication link between the smart phone 762 and the injector system control module 302 in order for the injector module 200" to be operable for at least performing programmed injections (e.g., the injector module 200" may be operable in one or more other respects without an established communication ink between the smart phone 762 and the injector system control module 302). The contrast media injector system 800" may be configured to require an established communication link between the smart phone 762 and the injector system control module 302 in order for the injector module 200" to be fully operable. The contrast media injector system 800" may be configured to require an established communication link between the smart phone 762 and the injector system control module 302 in order for the injector module 200" to be operable in any respect.

The smart phone 762 may be used with multiple injector modules 200" (e.g., the smart phone 762 could replace the tablet computer 700 in the FIG. 9 configuration, and the injector module 200" could replace the injector modules 200c in the FIG. 9 configuration). All signals that ultimately control operation of the powerhead 300 in the injector system 800" may be transmitted from or through the injector system control module 302. For instance, the contrast media injector system 800" may utilize a master/slave control architecture, where the powerhead 300 (more specifically the injector system control module 302) of the injector system 800" is the "master" and where each smart phone 762 is a "slave." The powerhead 300 (more specifically the injector system control module 302) of the injector system 800" may be characterized as a master node in a control architecture, while each smart phone 762 may be characterized as a requestor node. Although inputs may be provided to the injector system 800" through one or more smart phones 762, these inputs are provided to the injector system control module 302 to control operation of its powerhead 300.

Figure 12:
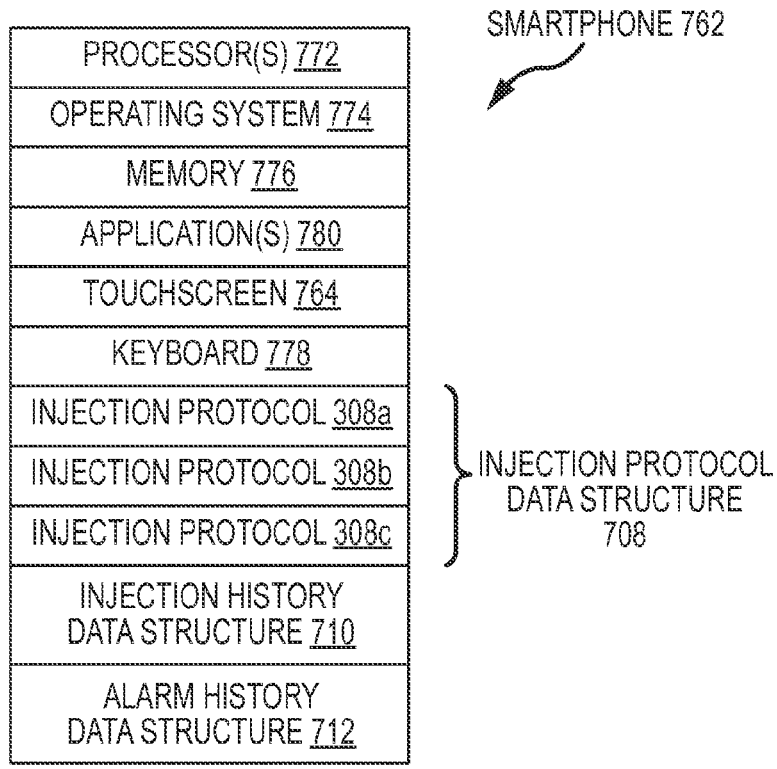
FIG. 12 is a block diagram of one embodiment of a smart phone that may be incorporated by a contrast media injector system.

A functional schematic for one embodiment of the smart phone 762 is presented in FIG. 12. The smart phone 760 includes one or more processors 772, an operating system 774 of any appropriate type (iOS, Android, Windows), memory 776 of any appropriate type or types (e.g., a computer-readable storage medium), and the above-noted touchscreen 764. The touchscreen 764 may incorporate an electronic keyboard. The smart phone 762 may include an optional physical keyboard 778 (e.g., a Qwerty keyboard). One or more apps or applications 780 may be stored on and/or utilized by the smart phone 762 (e.g., in memory 776), including for purposes of interfacing with the injector module 200". The smart phone 762 may also include the above-noted injection protocol data structure 708, injection history data structure 710, and alarm history data structure 712. Each of these data structures 708, 710, and 712 may be configured/stored in the memory 776 of the smart phone 762.

Multiple injection protocols 308 may be stored by the smart phone 762 of the injector system 800", namely in the injection protocol data structure 708. It may be such that only a single injection protocol 308 is stored on the powerhead 300 in the case of the injector system 800". The powerhead 300 does not incorporate the injection protocol data structure 708 in the case of the injector system 800". However, the powerhead 300 (through the injector system control module 302) of the injector system 800" may retrieve an injection protocol 308 stored in the injection protocol data structure 708 of the smart phone 762, and may then retain this single injection protocol 308 in its memory to control operation of the powerhead 300.

The injection history data structure 710 for the smart phone 762 of the injector system 800" includes data from multiple executions of one or more of the injection protocols 308 from the corresponding injection protocol data structure 708. These "multiple executions" could be of the same injection protocol 308 from the corresponding injection protocol data structure 708. These "multiple executions" could be at least one execution of two or more of the injection protocols 308 from the corresponding injection protocol data structure 708. In one embodiment, data on the most recent "x" injection protocols 308 from the injection protocol data structure 708 that were executed by the injector system 800" are stored in the injection history data structure 710 of the smart phone 762 (where "x" is an appropriate integer). The injection history data structure 710 is not incorporated by the powerhead 300 in the case of the injector system 800".

The alarm history data structure 712 for the smart phone 762 of the injector system 800" includes data relating to alarm conditions that were encountered during the execution of one or more of the injection protocols 308 from the corresponding injection protocol data structure 708. In one embodiment, data on the most recent "x" alarm conditions are stored in the alarm history data structure 712 of the smart phone 762 (where "x" is an appropriate integer). The alarm history data structure 712 is not incorporated by the powerhead 300 in the case of the injector system 800".

Figure 13:
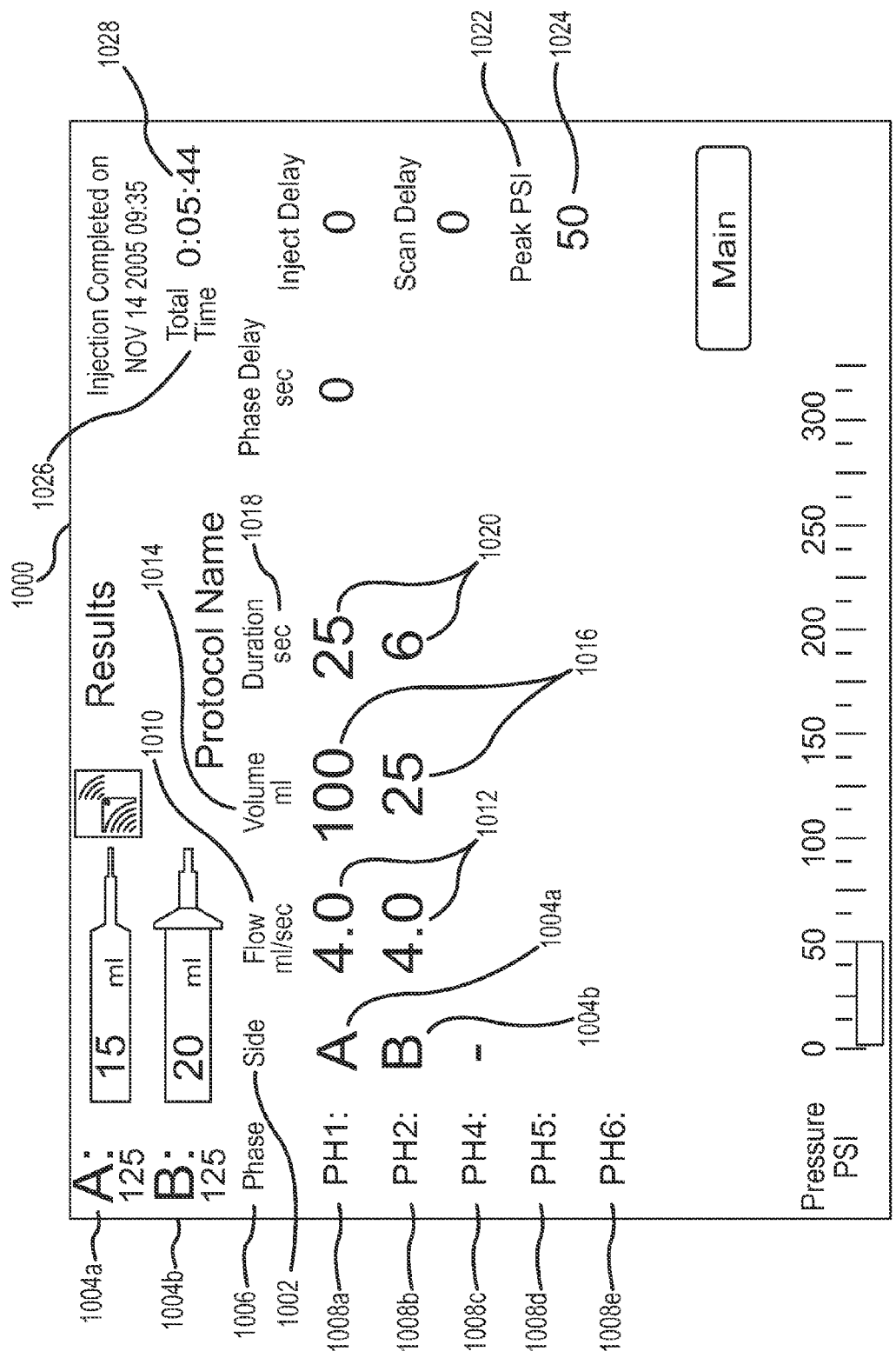
FIG. 13 is one embodiment of a results screen that may be displayed on a tablet computer and/or smart phone of a contrast media injector system.

FIG. 13 presents one embodiment of a results screen 1000. This results screen 1000 may be output onto the touchscreen 720 of any tablet computer 700 described herein (e.g., its display), onto the touchscreen 764 of any smart phone 762 described herein (e.g., its display), or both. Generally, the results screen 1000 provides information on the execution of an injection protocol 308 or any other fluid delivery procedure.

Two fluid sources 1004a and 1004b are shown as having been used for the execution of the injection protocol 308 corresponding with the illustrated results screen 1000. Results may of course be provided for injection protocols 308 that use any appropriate number of fluid sources. Moreover, although the fluid sources 1004a, 1004b are pictorially represented by syringes on the results screen 1000, any appropriate fluid source may be utilized and/or pictorially represented in any appropriate manner on the results screen 1000.

Any appropriate injection results information may be presented on the results screen 1000. In the illustrated embodiment, there is a phase designation 1006, a fluid source designation 1002 (e.g., an identification of the fluid source that was utilized for the associated phase), an achieved flow rate designation 1010 (e.g., the maximum flow rate achieved during the associated phase), an achieved volume designation 1014 (e.g., the fluid volume delivered during the associated phase), a phase duration designation 1018 (e.g., the total time required to execute the associated phase), a peak pressure designation 1022 (e.g., the maximum pressure achieved during execution of the injection protocol), and a total injection time designation 1026 (e.g., the total amount of time required for execution of the injection protocol). Data may be presented for any of these particular designations.

The results screen 1000 presents the results from execution of a two phase injection protocol (phases 1008a and 1008b). Results for any appropriate number phases (e.g., phases 1008a-e) may be presented. For each phase utilized by an injection protocol (phase 1008a and 1008b in the illustrated embodiment), the results screen 1000 presents the associated fluid source 1004a or 1004b, the achieved flow rate 1012, the achieved volume 1016, and the phase duration 1020. The results screen 1000 also presents the peak pressure 1024 that was achieved at some point in time during the execution of the injection protocol, as well as the total injection time 1028.

The injector systems 800, 800', 800c, and 800" have been described herein as including an injector module with a powerhead. This powerhead has been described as accommodating one or more syringes and that utilizes one or more syringe plunger drivers. However, it should be appreciated that injector modules of any appropriate configuration may be utilized by the injector systems 800, 800', 800c, and 800"

(e.g., an injector system that uses one or more tablet computers; an injector system that uses one or more smart phones). An injector module may deliver fluid in any appropriate manner for purposes of the injector systems 800, 800', 800c, and 800" (e.g., using one or more peristaltic pumps versus the type of syringe plunger driver described herein; a "syringe-less" configuration), including without limitation injector modules in accordance with the CT Exprse3D™ available from Swiss Medical Care SA of Lausanne, Switzerland, as well as injector modules in accordance with the CT Motion™, Mississippi™, Missouri™, Ohio Tandem™, Ohio M™, and Tennessee™ available from Ulrich Medical of Ulm, Germany.

It should be appreciated that any of the injector systems 800, 800', 800c, and 800" described herein may be adapted in any appropriate manner for multi-dosing/multi-patient applications (e.g., injector systems that use a bulk supply of at least one contrast media to accommodate multiple executions of one or more injection protocols, typically to different patients). For instance, the injector systems 800, 800', 800c, and 800" could use a multi-patient tubing set (used for multiple patients) that is detachably connected to a patient-specific or disposable tubing set (a patient-specific tubing set being used for only one patient). Multi-dosing/multi-patient injector system configurations of any appropriate type may use one or more tablet computers in accordance with the foregoing. Multi-patient injector system configurations of any appropriate type may use one or more smart phones in accordance with the foregoing.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed:

1. A contrast media injector system comprising:
   an injector module comprising:
      a drive source; and
      one or more tablet docking stations, wherein each said tablet docking station comprises a first docking connector;
   an injector system control module in communication with said drive source; and
   one or more tablet computers that are each in the form of a portable device and that are each operable when detachably mounted to said injector module via a corresponding said tablet docking station and also when detachably dismounted from said injector module, wherein said one or more tablet computers comprises a first tablet computer, wherein each said tablet computer comprises a second docking connector;
   wherein each said tablet computer of said contrast media injector system is disposable in each of a docked configuration and an undocked configuration relative to said injector module, wherein each said tablet computer of said contrast media injector system is a given tablet computer and where:
      said docked configuration is where said given tablet computer is physically connected to one said tablet docking station of said injector module and with its corresponding said second docking connector being interfaced with a corresponding said first docking connector of said injector module; and
      said undocked configuration is where said given tablet computer is physically disconnected from each said tablet docking station of said injector module and with its corresponding said second docking connector not being interfaced with any said first docking connector of said injector module;
   wherein each said tablet computer of said contrast media injector system is separately movable between its corresponding said docked and undocked configurations, wherein each said tablet computer of said contrast media injector system becomes part of said injector module only when in its corresponding said docked configuration, wherein said injector system is configured to require an established communication link between said first tablet computer and said injector system control module in order for said injector module to be operable for a least performing a programmed injection and including when no said tablet computer of said contrast media injector system is in said docked configuration and also when said first tablet computer is in said docked configuration, wherein all user inputs to said injector system control module are required to be provided only through at least one said tablet computer of said contrast media injector system, wherein said first tablet computer may be used to program an injection protocol, to initiate an injection by said contrast media injector system, and to terminate execution of said injection by said contrast media injector system, and wherein a communication link is establishable between said injector system control module and each said tablet computer of said contrast media injector system when in both of said docked and undocked configurations.

2. The injector system of claim 1, wherein said injector module further comprises a support and a powerhead movably interconnected with said support.

3. The injector system of claim 2, wherein said powerhead comprises said injector system control module.

4. The injector system of claim 2, wherein only a single user input device is available for communicating with said injector system control module when said first tablet computer is in said docked configuration, and wherein said single user input device is said first tablet computer.

5. The injector system of claim 2, wherein said powerhead comprises said injector system control module, and wherein all user inputs to said injector system control module are required to be entered through said first tablet computer.

6. The injector system of claim 2, wherein only a single touchscreen is available for providing user input to said injector system control module when said first tablet computer is in said docked configuration, and wherein said first tablet computer comprises said single touchscreen.

7. The injector system of claim 1, wherein having said established communication link between said first tablet computer and said injector system control module is required for said injector module to be operable in any respect.

8. The injector system of claim 1, wherein having said established communication link between said first tablet computer and said injector system control module is required for said injector module to be fully operable.

9. The injector system of claim 1, wherein said injector system has a single user input device in the form of said first tablet computer.

10. The injector system of claim 1, further comprising:
a plurality of said tablet computers that are each in communication with said injector system control module.

11. The injector system of claim 1, further comprising:
a plurality of said tablet docking stations, wherein each said tablet computer of said contrast media injector system is both dockable to and removable from each of said plurality of said tablet docking stations.

12. The injector system of claim 11, wherein said plurality of said tablet docking stations comprises a first tablet docking station and a second tablet docking station, wherein said injector module and said first tablet docking station are located in a first room, and wherein said second tablet docking station is located in a different second room.

13. The injector system of claim 12, further comprising:
a second tablet computer in communication with said injector system control module, wherein said first tablet computer is dedicated to said first tablet docking station, and wherein said second said tablet computer is dedicated to said second tablet docking station.

14. The injector system of claim 1, further comprising:
a plurality of said injector modules, wherein each said tablet computer of said contrast media injector system is configured to communicate with each of said injector modules.

15. The injector system of claim 1, further comprising:
a user-mountable user input device in communication with said first tablet computer, wherein said user-mountable user input device comprises at least one user mounting connector.

16. The injector system of claim 1, wherein said injector module comprises a powerhead, wherein said powerhead comprises said injector system control module, wherein said injector system further comprises a master/slave control architecture, wherein said powerhead is a master node for said master/slave control architecture, and wherein said first tablet computer is a slave node for said master/slave control architecture.

17. The injector system of claim 16, wherein said powerhead comprises a single stored injection protocol, and wherein said first tablet computer comprises a plurality of stored injection protocols.

18. The injector system of claim 16, further comprising:
an injection protocol data structure that comprises a plurality of injection protocols, wherein an entirety of said injection protocol data structure is stored on said first tablet computer and none of said injection protocol data structure is stored on said powerhead.

19. The injector system of claim 16, further comprising:
an injection history data structure, wherein an entirety of said injection history data structure is stored on said first tablet computer and none of said injection history data structure is stored on said powerhead.

20. The injector system of claim 16, further comprising:
an alarm history data structure, wherein an entirety of said alarm history data structure is stored on said first tablet computer and none of said alarm history data structure is stored on said powerhead.

21. The injector system of claim 1, wherein injection results are displayed on said first tablet computer.

* * * * *